US010898063B2

(12) United States Patent
Kirma et al.

(10) Patent No.: US 10,898,063 B2
(45) Date of Patent: Jan. 26, 2021

(54) FLEXIBLE ELECTRONIC CIRCUIT BOARD FOR A MULTI CAMERA ENDOSCOPE

(71) Applicant: EndoChoice Innovation Center Ltd., Caesarea (IL)

(72) Inventors: Yaniv Kirma, Tzrufa (IL); Moshe Levi, Ganey Tikva (IL); Amram Aizenfeld, Ramot Menashe (IL)

(73) Assignee: EndoChoice, Inc., Alpharetta, GA (US)

(*) Notice: Subject to any disclaimer, the term of this patent is extended or adjusted under 35 U.S.C. 154(b) by 0 days.

(21) Appl. No.: 15/730,202

(22) Filed: Oct. 11, 2017

(65) Prior Publication Data
US 2018/0028053 A1   Feb. 1, 2018

Related U.S. Application Data

(63) Continuation of application No. 13/992,014, filed as application No. PCT/IL2011/050049 on Dec. 8, 2011, now Pat. No. 9,814,374.
(Continued)

(51) Int. Cl.
*A61B 1/00* (2006.01)
*A61B 1/04* (2006.01)
(Continued)

(52) U.S. Cl.
CPC .......... *A61B 1/042* (2013.01); *A61B 1/00091* (2013.01); *A61B 1/00094* (2013.01);
(Continued)

(58) Field of Classification Search
CPC ............ A61B 1/00091; A61B 1/00094; A61B 1/00096; A61B 1/00177; A61B 1/042;
(Continued)

(56) References Cited

U.S. PATENT DOCUMENTS 3,639,714 A  2/1972 Fujimoto
3,955,064 A  5/1976 Demetrio
(Continued)

FOREIGN PATENT DOCUMENTS

CN  1376443    10/2002
CN  2829646 Y  10/2006
(Continued)

OTHER PUBLICATIONS

Anonymous, "Flex Circuit Design Guide" by Minico, Technical Specification FC302, http://www-eng.lbl.gov/~shuman/NEXT/CURRENT_DESIGN/TP/MATERIALS/flex_design_minco.pdf.*
(Continued)

*Primary Examiner* — James T Boylan
(74) *Attorney, Agent, or Firm* — Bookoff McAndrews, PLLC

(57) ABSTRACT

There is provided herein a flexible electronic circuit board for a tip section of a multi-camera endoscope, the circuit board comprising a front camera surface configured to carry a forward looking camera, a first side camera surface configured to carry a first side looking camera, a second side camera surface configured to carry a second side looking camera, one or more front illuminator surfaces a configured to carry one or more front illuminators to essentially illuminate the FOV of the forward looking camera, one or more side illuminator surfaces configured to carry one or more side illuminators to essentially illuminate the FOV of the first side looking camera and one or more side illuminator surfaces configured to carry one or more side illuminators to essentially illuminate the FOV of the second side looking camera.

20 Claims, 8 Drawing Sheets

Related U.S. Application Data

(60) Provisional application No. 61/421,238, filed on Dec. 9, 2010.

(51) Int. Cl.
   *A61B 1/05* (2006.01)
   *H04N 5/225* (2006.01)

(52) U.S. Cl.
   CPC ...... *A61B 1/00096* (2013.01); *A61B 1/00177* (2013.01); *A61B 1/05* (2013.01); *H04N 5/2253* (2013.01); *H04N 5/2256* (2013.01); *H04N 5/2258* (2013.01); *H04N 2005/2255* (2013.01)

(58) Field of Classification Search
   CPC ... A61B 1/05; A61B 1/00052; A61B 1/00064; A61B 1/00071; A61B 1/00119; A61B 1/012; A61B 1/0676; A61B 1/00181; A61B 1/018; H04N 5/2256; H04N 5/2252; H04N 5/2253; H04N 2005/2255
   USPC .......................................................... 348/76
   See application file for complete search history.

(56) References Cited

U.S. PATENT DOCUMENTS

| | | |
|---|---|---|
| 4,037,588 A | 7/1977 | Heckele |
| 4,084,401 A | 4/1978 | Belardi |
| 4,253,448 A | 3/1981 | Terada |
| 4,261,345 A | 4/1981 | Yamaguchi |
| 4,402,313 A | 9/1983 | Yabe |
| 4,414,608 A | 11/1983 | Furihata |
| 4,439,030 A | 3/1984 | Ueda |
| 4,469,090 A | 9/1984 | Konomura |
| 4,494,549 A | 1/1985 | Namba |
| 4,522,196 A | 6/1985 | Cunningham |
| 4,565,423 A | 1/1986 | Ueda |
| 4,576,144 A | 3/1986 | Ishii |
| 4,588,294 A | 5/1986 | Siegmund |
| 4,590,923 A | 5/1986 | Watanabe |
| 4,641,635 A | 2/1987 | Yabe |
| 4,699,463 A | 10/1987 | D |
| 4,708,126 A | 11/1987 | Toda |
| 4,727,859 A | 3/1988 | Lia |
| 4,736,732 A | 4/1988 | Shimonaka |
| 4,753,222 A | 6/1988 | Morishita |
| 4,764,001 A | 8/1988 | Yokota |
| 4,794,913 A | 1/1989 | Shimonaka |
| 4,801,792 A | 1/1989 | Yamasita |
| 4,841,952 A | 6/1989 | Sato |
| 4,846,154 A | 7/1989 | MacAnally |
| 4,868,644 A | 9/1989 | Yabe |
| 4,877,314 A | 10/1989 | Kanamori |
| 4,878,485 A | 11/1989 | Adair |
| 4,888,639 A | 12/1989 | Yabe |
| 4,902,115 A | 2/1990 | Takahashi |
| 4,905,670 A | 3/1990 | Adair |
| 4,914,521 A | 4/1990 | Adair |
| 4,974,075 A | 11/1990 | Nakajima |
| 4,976,522 A | 12/1990 | Igarashi |
| 4,982,724 A | 1/1991 | Saito |
| 4,984,878 A | 1/1991 | Miyano |
| 4,998,182 A | 3/1991 | Krauter |
| 5,166,787 A | 11/1992 | Irion |
| 5,193,525 A | 3/1993 | Silverstein |
| 5,239,983 A | 8/1993 | Katsurada |
| 5,296,971 A | 3/1994 | Mori |
| 5,299,561 A | 4/1994 | Yoshimoto |
| 5,305,121 A | 4/1994 | Moll |
| 5,309,227 A | 5/1994 | Inoue |
| 5,313,934 A | 5/1994 | Wiita |
| 5,339,800 A | 8/1994 | Wiita |
| 5,359,456 A | 10/1994 | Kikuchi |
| 5,380,049 A | 1/1995 | Smowton |
| 5,398,056 A | 3/1995 | Yabe |
| 5,408,623 A | 4/1995 | Dolidon |
| 5,412,478 A | 5/1995 | Ishihara |
| 5,420,644 A | 5/1995 | Watanabe |
| 5,432,543 A | 7/1995 | Hasegawa |
| 5,436,767 A | 7/1995 | Suzuki |
| 5,447,148 A | 9/1995 | Oneda |
| 5,452,391 A | 9/1995 | Chou |
| 5,460,167 A | 10/1995 | Yabe |
| 5,475,420 A | 12/1995 | Buchin |
| 5,483,951 A | 1/1996 | Frassica |
| 5,485,316 A | 1/1996 | Mori |
| 5,489,256 A | 2/1996 | Adair |
| 5,507,717 A | 4/1996 | Kura |
| 5,512,940 A | 4/1996 | Takasugi |
| 5,515,449 A | 5/1996 | Tsuruoka |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,550,582 A | 8/1996 | Takasugi |
| 5,585,840 A | 12/1996 | Watanabe |
| 5,587,839 A | 12/1996 | Miyano |
| 5,589,874 A | 12/1996 | Buchin |
| 5,592,216 A | 1/1997 | Uehara |
| 5,605,530 A | 2/1997 | Fischell |
| 5,609,560 A | 3/1997 | Ichikawa |
| 5,617,136 A | 4/1997 | Iso |
| 5,630,782 A | 5/1997 | Adair |
| 5,653,677 A | 8/1997 | Okada |
| 5,656,011 A | 8/1997 | Uihlein |
| 5,662,588 A | 9/1997 | Iida |
| 5,675,378 A | 10/1997 | Takasugi |
| 5,679,110 A | 10/1997 | Hamazaki |
| 5,685,823 A | 11/1997 | Ito |
| 5,701,155 A | 12/1997 | Wood |
| 5,702,345 A | 12/1997 | Wood |
| 5,702,347 A | 12/1997 | Yabe |
| 5,707,344 A | 1/1998 | Nakazawa |
| 5,716,323 A | 2/1998 | Lee |
| 5,725,474 A | 3/1998 | Yasui |
| 5,725,476 A | 3/1998 | Yasui |
| 5,725,477 A | 3/1998 | Yasui |
| 5,728,045 A | 3/1998 | Komi |
| 5,751,340 A | 5/1998 | Strobl |
| 5,764,809 A | 6/1998 | Nomami |
| 5,777,797 A | 7/1998 | Miyano |
| 5,782,751 A | 7/1998 | Matsuno |
| 5,793,539 A | 8/1998 | Konno |
| 5,800,341 A | 9/1998 | McKenna |
| 5,812,187 A | 9/1998 | Watanabe |
| 5,826,126 A * | 10/1998 | Nomura .................. G02B 7/08 396/542 |
| 5,830,124 A | 11/1998 | Suzuki |
| 5,836,894 A | 11/1998 | Sarvazyan |
| 5,852,511 A | 12/1998 | Tateyama |
| 5,860,913 A | 1/1999 | Yamaya |
| 5,870,234 A | 2/1999 | Ebbesmeier nee Schitthof |
| 5,871,439 A | 2/1999 | Takahashi |
| 5,871,440 A | 2/1999 | Okada |
| 5,876,326 A | 3/1999 | Takamura |
| 5,879,284 A | 3/1999 | Tsujita |
| 5,894,322 A | 4/1999 | Hamano |
| 5,912,764 A | 6/1999 | Togino |
| 5,913,817 A | 6/1999 | Lee |
| 5,914,810 A | 6/1999 | Watts |
| 5,916,148 A | 6/1999 | Tsuyuki |
| 5,929,901 A | 7/1999 | Adair |
| 5,930,424 A | 7/1999 | Heimberger |
| 5,933,275 A | 8/1999 | Igarashi |
| 5,933,282 A | 8/1999 | Tomioka |
| 5,936,773 A | 8/1999 | Togino |
| 5,940,126 A | 8/1999 | Kimura |
| 5,961,445 A | 10/1999 | Chikama |
| 5,969,888 A | 10/1999 | Sukekawa |
| 5,986,693 A | 11/1999 | Adair |
| 5,989,185 A | 11/1999 | Miyazaki |
| 5,993,037 A | 11/1999 | Tomioka |
| 5,995,136 A | 11/1999 | Hattori |

(56) References Cited

U.S. PATENT DOCUMENTS

| | | |
|---|---|---|
| 6,009,189 A | 12/1999 | Schaack |
| 6,025,873 A | 2/2000 | Nishioka |
| 6,043,839 A | 3/2000 | Adair |
| 6,069,698 A | 5/2000 | Ozawa |
| 6,080,104 A | 6/2000 | Ozawa |
| 6,104,540 A | 8/2000 | Hayakawa |
| 6,110,127 A | 8/2000 | Suzuki |
| 6,117,068 A | 9/2000 | Gourley |
| 6,124,989 A | 9/2000 | Oode |
| 6,139,175 A | 10/2000 | Tomioka |
| 6,139,490 A | 10/2000 | Breidenthal |
| 6,147,808 A | 11/2000 | Togino |
| 6,163,401 A | 12/2000 | Igarashi |
| 6,166,858 A | 12/2000 | Togino |
| 6,181,481 B1 | 1/2001 | Yamamoto |
| 6,184,923 B1 | 2/2001 | Miyazaki |
| 6,185,046 B1 | 2/2001 | Togino |
| 6,196,967 B1 | 3/2001 | Lim |
| 6,201,646 B1 | 3/2001 | Togino |
| 6,201,648 B1 | 3/2001 | Togino |
| 6,210,322 B1 | 4/2001 | Byrne |
| 6,211,904 B1 | 4/2001 | Adair |
| 6,215,517 B1 | 4/2001 | Takahashi |
| 6,217,500 B1 | 4/2001 | Helseth |
| 6,245,086 B1 | 6/2001 | Storz |
| 6,249,391 B1 | 6/2001 | Hayakawa |
| 6,260,994 B1 | 7/2001 | Matsumoto |
| 6,261,226 B1 | 7/2001 | McKenna |
| 6,275,255 B1 | 8/2001 | Adair |
| 6,295,368 B1 | 9/2001 | Hasegawa |
| 6,306,082 B1 | 10/2001 | Takahashi |
| 6,310,642 B1 | 10/2001 | Adair |
| 6,310,736 B1 | 10/2001 | Togino |
| 6,315,712 B1 | 11/2001 | Rovegno |
| 6,322,496 B1 | 11/2001 | Iida |
| 6,327,094 B1 | 12/2001 | Aoki |
| 6,327,101 B1 | 12/2001 | Miyano |
| 6,334,845 B1 | 1/2002 | Higuchi |
| 6,353,504 B1 | 3/2002 | Yamamoto |
| 6,375,610 B2 | 4/2002 | Verschuur |
| 6,387,045 B1 | 5/2002 | Takahashi |
| 6,398,723 B1 | 6/2002 | Kehr |
| 6,400,514 B2 | 6/2002 | Minami |
| 6,422,995 B2 | 7/2002 | Akiba |
| 6,425,857 B1 | 7/2002 | Rudischhauser |
| 6,450,950 B2 | 9/2002 | Irion |
| 6,461,304 B1 | 10/2002 | Tanaka |
| 6,464,631 B1 | 10/2002 | Girke |
| 6,464,633 B1 | 10/2002 | Hosoda |
| 6,468,201 B1 | 10/2002 | Burdick |
| 6,468,202 B1 | 10/2002 | Irion |
| 6,471,636 B1 | 10/2002 | Sano |
| 6,471,637 B1 | 10/2002 | Green |
| 6,473,116 B1 | 10/2002 | Takahashi |
| 6,476,851 B1 | 11/2002 | Nakamura |
| 6,500,115 B2 | 12/2002 | Krattiger |
| 6,514,210 B2 | 2/2003 | Ohara |
| 6,520,908 B1 | 2/2003 | Ikeda |
| 6,527,704 B1 | 3/2003 | Chang |
| 6,530,881 B1 | 3/2003 | Ailinger |
| 6,533,722 B2 | 3/2003 | Nakashima |
| 6,545,703 B1 | 4/2003 | Takahashi |
| 6,551,239 B2 | 4/2003 | Renner |
| 6,554,767 B2 | 4/2003 | Tanaka |
| 6,567,114 B2 | 5/2003 | Takahashi |
| 6,569,084 B1 | 5/2003 | Mizuno |
| 6,582,361 B2 | 6/2003 | Hirano |
| 6,589,168 B2 | 7/2003 | Thompson |
| 6,606,113 B2 | 8/2003 | Nakamura |
| 6,618,205 B2 | 9/2003 | Murayama |
| D481,125 S | 10/2003 | Hayamizu |
| 6,638,212 B1 | 10/2003 | Oshima |
| 6,638,214 B2 | 10/2003 | Akiba |
| 6,641,531 B2 | 11/2003 | Kehr |
| 6,656,111 B2 | 12/2003 | Fujii |
| 6,671,099 B2 | 12/2003 | Nagata |
| 6,677,983 B1 | 1/2004 | Takahashi |
| 6,677,984 B2 | 1/2004 | Kobayashi |
| 6,677,992 B1 | 1/2004 | Matsumoto |
| 6,692,430 B2 | 2/2004 | Adler |
| 6,692,431 B2 | 2/2004 | Kazakevich |
| 6,699,181 B2 | 3/2004 | Wako |
| 6,699,185 B2 | 3/2004 | Gminder |
| 6,704,052 B1 | 3/2004 | Togino |
| 6,712,760 B2 | 3/2004 | Sano |
| D490,898 S | 6/2004 | Hayamizu |
| 6,764,439 B2 | 7/2004 | Schaaf |
| 6,778,208 B2 | 8/2004 | Takeshige |
| 6,788,343 B1 | 9/2004 | Togino |
| 6,793,621 B2 | 9/2004 | Butler |
| 6,801,325 B2 | 10/2004 | Farr |
| 6,809,499 B2 | 10/2004 | Solingen |
| 6,809,866 B2 | 10/2004 | Xie |
| 6,829,003 B2 | 12/2004 | Takami |
| 6,832,984 B2 | 12/2004 | Stelzer |
| 6,844,985 B2 | 1/2005 | Murayama |
| 6,846,311 B2 | 1/2005 | Gatto |
| 6,849,043 B2 | 2/2005 | Kondo |
| 6,860,516 B2 | 3/2005 | Ouchi |
| 6,876,380 B2 | 4/2005 | Abe |
| 6,887,194 B2 | 5/2005 | Hart |
| 6,888,119 B2 | 5/2005 | Iizuka |
| 6,898,086 B2 | 5/2005 | Takami |
| 6,899,673 B2 | 5/2005 | Ogura |
| 6,900,829 B1 | 5/2005 | Ozawa |
| 6,900,950 B2 | 5/2005 | Nagata |
| 6,902,529 B2 | 6/2005 | Onishi |
| 6,903,761 B1 | 6/2005 | Abe |
| 6,918,693 B2 | 7/2005 | Ota |
| 6,921,362 B2 | 7/2005 | Ouchi |
| 6,930,705 B2 | 8/2005 | Tanaka |
| 6,933,962 B2 | 8/2005 | Yamamoto |
| 6,937,267 B1 | 8/2005 | Takahashi |
| 6,937,269 B2 | 8/2005 | Sugimoto |
| 6,943,821 B2 | 9/2005 | Abe |
| 6,943,822 B2 | 9/2005 | Iida |
| 6,944,031 B2 | 9/2005 | Takami |
| 6,945,929 B2 | 9/2005 | Ando |
| 6,947,070 B2 | 9/2005 | Takami |
| 6,950,691 B2 | 9/2005 | Uchikubo |
| 6,956,703 B2 | 10/2005 | Saito |
| 6,967,673 B2 | 11/2005 | Ozawa |
| 6,977,670 B2 | 12/2005 | Takahashi |
| 6,980,227 B2 | 12/2005 | Iida |
| 6,982,740 B2 | 1/2006 | Adair |
| 6,985,170 B1 | 1/2006 | Tsuyuki |
| 6,992,694 B2 | 1/2006 | Abe |
| 6,995,786 B2 | 2/2006 | Abe |
| 6,997,871 B2 | 2/2006 | Sonnenschein |
| 7,027,231 B2 | 4/2006 | Miyano |
| 7,030,904 B2 | 4/2006 | Adair |
| 7,037,258 B2 | 5/2006 | Chatenever |
| 7,042,488 B2 | 5/2006 | Higuchi |
| 7,043,153 B2 | 5/2006 | Takeyama |
| 7,046,270 B2 | 5/2006 | Murata |
| 7,050,086 B2 | 5/2006 | Ozawa |
| 7,074,181 B2 | 7/2006 | Futatsugi |
| 7,074,182 B2 | 7/2006 | Rovegno |
| 7,085,064 B2 | 8/2006 | Uzawa |
| 7,097,615 B2 | 8/2006 | Banik |
| 7,104,951 B2 | 9/2006 | Hasegawa |
| 7,108,656 B2 | 9/2006 | Fujikawa |
| 7,108,657 B2 | 9/2006 | Irion |
| 7,119,830 B2 | 10/2006 | Saito |
| 7,123,288 B2 | 10/2006 | Abe |
| 7,128,709 B2 | 10/2006 | Saruya |
| 7,129,472 B1 | 10/2006 | Okawa |
| 7,133,063 B2 | 11/2006 | Abe |
| D534,656 S | 1/2007 | Pilvisto |
| 7,156,863 B2 | 1/2007 | Sonnenschein |
| 7,158,314 B2 | 1/2007 | Fujii |
| 7,179,221 B2 | 2/2007 | Tsujita |
| 7,180,686 B2 | 2/2007 | Kato |
| 7,218,454 B2 | 5/2007 | Miyano |

(56) References Cited

U.S. PATENT DOCUMENTS

| | | |
|---|---|---|
| 7,223,231 B2 | 5/2007 | Akiba |
| 7,231,135 B2 | 6/2007 | Esenyan |
| 7,232,409 B2 | 6/2007 | Hale |
| 7,233,820 B2 | 6/2007 | Gilboa |
| 7,242,833 B2 | 7/2007 | Yang |
| 7,248,281 B2 | 7/2007 | Abe |
| 7,248,296 B2 | 7/2007 | Iketani |
| 7,252,633 B2 | 8/2007 | Obata |
| 7,255,676 B2 | 8/2007 | Higuchi |
| 7,262,797 B2 | 8/2007 | Weldum |
| 7,267,647 B2 | 9/2007 | Okada |
| 7,273,452 B2 | 9/2007 | Barbato |
| 7,277,120 B2 | 10/2007 | Gere |
| 7,280,140 B2 | 10/2007 | Henderson |
| 7,280,283 B1 | 10/2007 | Kasai |
| 7,282,025 B2 | 10/2007 | Abe |
| 7,306,588 B2 | 12/2007 | Loeb |
| 7,330,749 B1 | 2/2008 | Bhunachet |
| D564,659 S | 3/2008 | Hayashi |
| D564,660 S | 3/2008 | Hayashi |
| 7,351,202 B2 | 4/2008 | Long |
| 7,355,625 B1 | 4/2008 | Mochida |
| 7,358,987 B2 | 4/2008 | Takeshige |
| 7,365,768 B1 | 4/2008 | Ono |
| 7,371,211 B2 | 5/2008 | Akiba |
| 7,379,252 B2 | 5/2008 | Murayama |
| 7,384,308 B2 | 6/2008 | Boehnlein |
| 7,399,304 B2 | 7/2008 | Gambale |
| 7,400,341 B2 | 7/2008 | Abe |
| 7,401,984 B2 | 7/2008 | Pattie |
| 7,409,130 B2 | 8/2008 | Hatori |
| 7,420,586 B2 | 9/2008 | Higuchi |
| 7,427,263 B2 | 9/2008 | Hoeg |
| 7,431,619 B2 | 10/2008 | Boehnlein |
| 7,435,217 B2 | 10/2008 | Wiklof |
| 7,435,218 B2 | 10/2008 | Krattiger |
| 7,440,005 B2 | 10/2008 | Enomoto |
| 7,443,488 B2 | 10/2008 | Ogawa |
| 7,450,151 B2 | 11/2008 | Kaneko |
| 7,466,490 B2 | 12/2008 | Igarashi |
| 7,471,310 B2 | 12/2008 | Amling |
| 7,484,709 B2 | 2/2009 | Efinger |
| 7,486,449 B2 | 2/2009 | Miyano |
| 7,492,388 B2 | 2/2009 | Odlivak |
| 7,514,667 B2 | 4/2009 | Matsumoto |
| 7,518,632 B2 | 4/2009 | Konomura |
| 7,530,948 B2 | 5/2009 | Seibel |
| 7,542,069 B2 | 6/2009 | Tashiro |
| 7,553,276 B2 | 6/2009 | Iddan |
| 7,559,889 B2 | 7/2009 | Takahashi |
| 7,559,892 B2 | 7/2009 | Adler |
| 7,561,351 B2 | 7/2009 | Konno |
| 7,569,012 B2 | 8/2009 | Tanaka |
| 7,573,499 B2 | 8/2009 | Doguchi |
| 7,576,310 B2 | 8/2009 | Konno |
| 7,581,968 B1 | 9/2009 | Boehnlein |
| 7,582,055 B2 | 9/2009 | Komiya |
| 7,582,056 B2 | 9/2009 | Noguchi |
| 7,584,534 B2 | 9/2009 | Pease |
| 7,585,274 B2 | 9/2009 | Homma |
| 7,588,535 B2 | 9/2009 | Adler |
| 7,593,051 B2 | 9/2009 | Suda |
| 7,621,868 B2 | 11/2009 | Breidenthal |
| 7,621,869 B2 | 11/2009 | Ratnakar |
| 7,623,150 B2 | 11/2009 | Kobayashi |
| 7,627,189 B2 | 12/2009 | Donomae |
| 7,630,148 B1 | 12/2009 | Yang |
| 7,671,888 B2 | 3/2010 | Nogami |
| 7,683,927 B2 | 3/2010 | Higuchi |
| 7,695,429 B2 | 4/2010 | Hino |
| 7,699,772 B2 | 4/2010 | Pauker |
| 7,701,650 B2 | 4/2010 | Lin |
| 7,725,013 B2 | 5/2010 | Sugimoto |
| 7,728,867 B2 | 6/2010 | Fukuyama |
| 7,734,160 B2 | 6/2010 | Sudo |
| 7,746,566 B2 | 6/2010 | Mizusawa |
| 7,746,572 B2 | 6/2010 | Asami |
| 7,749,156 B2 | 7/2010 | Ouchi |
| 7,749,159 B2 | 7/2010 | Crowley |
| 7,758,495 B2 | 7/2010 | Pease |
| 7,758,499 B2 | 7/2010 | Adler |
| 7,772,786 B2 | 8/2010 | Hosoda |
| 7,773,110 B2 | 8/2010 | Abe |
| 7,773,122 B2 | 8/2010 | Irion |
| 7,773,318 B2 | 8/2010 | Takato |
| 7,775,971 B2 | 8/2010 | Fujimori |
| 7,775,973 B2 | 8/2010 | Okada |
| 7,789,822 B2 | 9/2010 | Suzuki |
| 7,800,656 B2 | 9/2010 | Takeuchi |
| RE41,807 E | 10/2010 | Yokoi |
| 7,821,529 B2 | 10/2010 | Mochida |
| 7,837,614 B2 | 11/2010 | Segawa |
| 7,841,880 B2 | 11/2010 | Ikeda |
| 7,846,090 B2 | 12/2010 | Pilvisto |
| 7,852,513 B2 | 12/2010 | Donomae |
| 7,893,956 B2 | 2/2011 | Ayrenschmalz |
| 7,896,802 B2 | 3/2011 | Otawara |
| 7,901,352 B2 | 3/2011 | Minami |
| 7,907,168 B2 | 3/2011 | Eino |
| 7,907,170 B2 | 3/2011 | Watanabe |
| 7,907,352 B2 | 3/2011 | Miyano |
| 7,914,443 B2 | 3/2011 | Uchimura |
| 7,918,788 B2 | 4/2011 | Lin |
| 7,938,773 B2 | 5/2011 | Kawai |
| 7,940,296 B2 | 5/2011 | Ogino |
| 7,942,814 B2 | 5/2011 | Remijan |
| 7,951,068 B2 | 5/2011 | Kura |
| 7,967,745 B2 | 6/2011 | Gilad |
| 7,976,462 B2 | 7/2011 | Wright |
| 7,995,093 B2 | 8/2011 | Takeuchi |
| 7,998,064 B2 | 8/2011 | Otawara |
| 8,002,596 B2 | 8/2011 | Suzuki |
| 8,027,101 B2 | 9/2011 | Suda |
| 8,033,992 B2 | 10/2011 | Hino |
| 8,035,684 B2 | 10/2011 | Wakito |
| 8,038,600 B2 | 10/2011 | Uchiyama |
| 8,043,207 B2 | 10/2011 | Adams |
| 8,060,172 B2 | 11/2011 | Ishihara |
| 8,063,962 B2 | 11/2011 | Hagihara |
| 8,066,631 B2 | 11/2011 | Wimmer |
| 8,072,483 B2 | 12/2011 | Tomioka |
| 8,072,537 B2 | 12/2011 | Schwarz |
| 8,072,693 B2 | 12/2011 | Togino |
| 8,075,477 B2 | 12/2011 | Nakamura |
| 8,075,478 B2 | 12/2011 | Campos |
| 8,098,441 B2 | 1/2012 | Sasamoto |
| 8,100,920 B2 | 1/2012 | Gambale |
| 8,102,415 B2 | 1/2012 | Iriyama |
| 8,105,233 B2 | 1/2012 | AbouElKheir |
| 8,113,846 B2 | 2/2012 | Wallaker |
| 8,125,514 B2 | 2/2012 | Sekiguchi |
| 8,125,515 B2 | 2/2012 | Hibi |
| 8,130,454 B2 | 3/2012 | Nogochi |
| 8,135,192 B2 | 3/2012 | Matsuzaki |
| 8,135,454 B2 | 3/2012 | Daniels |
| 8,139,296 B2 | 3/2012 | Ito |
| 8,144,191 B2 | 3/2012 | Kawanishi |
| 8,149,274 B2 | 4/2012 | Yamazaki |
| 8,152,718 B2 | 4/2012 | Cheng |
| 8,152,821 B2 | 4/2012 | Gambale |
| 8,157,798 B2 | 4/2012 | Takahashi |
| 8,164,836 B2 | 4/2012 | Uzawa |
| 8,167,791 B2 | 5/2012 | Tanaka |
| 8,167,795 B2 | 5/2012 | Hoeg |
| 8,167,796 B2 | 5/2012 | Negishi |
| 8,182,419 B2 | 5/2012 | Kohno |
| 8,187,171 B2 | 5/2012 | Irion |
| 8,187,174 B2 | 5/2012 | Wang |
| 8,189,041 B2 | 5/2012 | Konishi |
| 8,189,062 B2 | 5/2012 | Irion |
| 8,194,380 B2 | 6/2012 | Murata |
| 8,197,400 B2 | 6/2012 | Boutillette |
| 8,200,042 B2 | 6/2012 | Doi |
| 8,208,015 B2 | 6/2012 | Unsai |

(56) References Cited

U.S. PATENT DOCUMENTS

| | | |
|---|---|---|
| 8,211,009 B2 | 7/2012 | Tanaka |
| 8,212,862 B2 | 7/2012 | Kase |
| 8,212,863 B2 | 7/2012 | Tanaka |
| 8,221,309 B2 | 7/2012 | Iida |
| 8,221,311 B2 | 7/2012 | Campos |
| 8,223,198 B2 | 7/2012 | Shibasaki |
| 8,228,369 B2 | 7/2012 | Kojima |
| 8,229,549 B2 | 7/2012 | Whitman |
| 8,235,942 B2 | 8/2012 | Frassica |
| 8,248,414 B2 | 8/2012 | Gattani |
| 8,262,558 B2 | 9/2012 | Sato |
| 8,262,565 B2 | 9/2012 | Okada |
| 8,279,275 B2 | 10/2012 | Gono |
| 8,295,566 B2 | 10/2012 | Nishimura |
| 8,300,325 B2 | 10/2012 | Katahira |
| 8,310,529 B2 | 11/2012 | Krupnick |
| 8,334,900 B2 | 12/2012 | Qu |
| 8,345,092 B2 | 1/2013 | Takasaki |
| 8,348,835 B2 | 1/2013 | Fujimori |
| 8,360,960 B2 | 1/2013 | Sasaki |
| 8,360,964 B2 | 1/2013 | Ertas |
| 8,366,623 B2 | 2/2013 | Misono |
| 8,382,673 B2 | 2/2013 | Nagano |
| 8,394,013 B2 | 3/2013 | Ichimura |
| 8,394,014 B2 | 3/2013 | Fuerst |
| 8,425,405 B2 | 4/2013 | Mitani |
| 8,435,173 B2 | 5/2013 | Hosaka |
| 8,439,829 B2 | 5/2013 | Miyamoto |
| 8,444,547 B2 | 5/2013 | Miyamoto |
| 8,444,548 B2 | 5/2013 | Kumei |
| 8,449,456 B2 | 5/2013 | Ueno |
| 8,449,457 B2 | 5/2013 | Aizenfeld |
| 8,456,562 B2 | 6/2013 | Ishii |
| 8,460,182 B2 | 6/2013 | Ouyang |
| 8,465,421 B2 | 6/2013 | Finkman |
| 8,480,670 B2 | 7/2013 | Sugita |
| 8,491,467 B2 | 7/2013 | Miyamoto |
| 8,520,919 B2 | 8/2013 | Stepp |
| 8,523,764 B2 | 9/2013 | Hatcher |
| 8,523,766 B2 | 9/2013 | Kudoh |
| 8,764,642 B2 | 7/2014 | Bendele |
| 9,144,373 B2 | 9/2015 | Kaye |
| 2002/0007110 A1 | 1/2002 | Irion |
| 2002/0087047 A1 | 7/2002 | Remijan |
| 2002/0098732 A1 | 7/2002 | Shimizu |
| 2002/0109771 A1 | 8/2002 | Ledbetter |
| 2002/0109774 A1 | 8/2002 | Meron |
| 2002/0151768 A1 | 10/2002 | Akiba |
| 2002/0161281 A1 | 10/2002 | Jaffe |
| 2002/0161282 A1 | 10/2002 | Fulghum |
| 2002/0183591 A1 | 12/2002 | Matsuura |
| 2003/0030918 A1 | 2/2003 | Murayama |
| 2003/0032860 A1 | 2/2003 | Avni |
| 2003/0036681 A1 | 2/2003 | Aviv |
| 2003/0055314 A1 | 3/2003 | Petitto |
| 2003/0083552 A1 | 5/2003 | Remijan |
| 2003/0125788 A1 | 7/2003 | Long |
| 2003/0130564 A1 | 7/2003 | Martone |
| 2003/0139648 A1 | 7/2003 | Foley |
| 2003/0158462 A1 | 8/2003 | Takase |
| 2003/0181787 A1 | 9/2003 | Kondo |
| 2003/0199860 A1 | 10/2003 | Loeb |
| 2004/0015049 A1 | 1/2004 | Zaar |
| 2004/0019347 A1 | 1/2004 | Sakurai |
| 2004/0024290 A1 | 2/2004 | Root |
| 2004/0034311 A1 | 2/2004 | Mihalcik |
| 2004/0073120 A1 | 4/2004 | Motz |
| 2004/0104999 A1 | 6/2004 | Okada |
| 2004/0111012 A1 | 6/2004 | Whitman |
| 2004/0133076 A1 | 7/2004 | Kobayashi |
| 2004/0138532 A1 | 7/2004 | Glukhovsky |
| 2004/0143162 A1 | 7/2004 | Krattiger |
| 2004/0158129 A1 | 8/2004 | Okada |
| 2004/0160682 A1 | 8/2004 | Miyano |
| 2004/0176661 A1 | 9/2004 | Futatsugi |
| 2004/0190159 A1 | 9/2004 | Hasegawa |
| 2004/0210113 A1 | 10/2004 | Hasegawa |
| 2004/0220451 A1 | 11/2004 | Gravenstein |
| 2004/0242958 A1 | 12/2004 | Fujikawa |
| 2004/0242961 A1 | 12/2004 | Bughici |
| 2004/0249247 A1 | 12/2004 | Iddan |
| 2004/0254423 A1 | 12/2004 | Wendlandt |
| 2004/0260151 A1 | 12/2004 | Akiba |
| 2004/0267093 A1 | 12/2004 | Miyagi |
| 2005/0020876 A1 | 1/2005 | Shioda |
| 2005/0027164 A1 | 2/2005 | Barbato |
| 2005/0038317 A1 | 2/2005 | Ratnakar |
| 2005/0038318 A1 | 2/2005 | Goldwasser |
| 2005/0043583 A1 | 2/2005 | Killmann |
| 2005/0080342 A1 | 4/2005 | Gilreath |
| 2005/0090709 A1 | 4/2005 | Okada |
| 2005/0096501 A1 | 5/2005 | Stelzer |
| 2005/0154255 A1 | 7/2005 | Jacobs |
| 2005/0154262 A1 | 7/2005 | Banik |
| 2005/0182295 A1 | 8/2005 | Soper |
| 2005/0203338 A1 | 9/2005 | Couvillon |
| 2005/0231476 A1* | 10/2005 | Armstrong ............ A63F 13/06 345/161 |
| 2005/0234296 A1 | 10/2005 | Saadat |
| 2005/0234347 A1 | 10/2005 | Yamataka |
| 2005/0251127 A1 | 11/2005 | Brosch |
| 2005/0256376 A1 | 11/2005 | Bar-Or |
| 2005/0261553 A1 | 11/2005 | Swain |
| 2005/0272975 A1 | 12/2005 | McWeeney |
| 2005/0283048 A1 | 12/2005 | Gill |
| 2005/0284491 A1 | 12/2005 | Tashiro |
| 2006/0004257 A1 | 1/2006 | Gilad |
| 2006/0047184 A1 | 3/2006 | Banik |
| 2006/0052663 A1 | 3/2006 | Koitabashi |
| 2006/0063976 A1 | 3/2006 | Aizenfeld |
| 2006/0069307 A1 | 3/2006 | Boulais |
| 2006/0069314 A1 | 3/2006 | Farr |
| 2006/0149129 A1 | 7/2006 | Watts |
| 2006/0173244 A1 | 8/2006 | Boulais |
| 2006/0183971 A1 | 8/2006 | Haviv |
| 2006/0183975 A1 | 8/2006 | Saadat et al. |
| 2006/0189845 A1 | 8/2006 | Maahs |
| 2006/0211916 A1 | 9/2006 | Kasahara |
| 2006/0217594 A1 | 9/2006 | Ferguson |
| 2006/0224040 A1 | 10/2006 | Khait |
| 2006/0229499 A1 | 10/2006 | Eisenkolb |
| 2006/0241347 A1 | 10/2006 | Whitehead |
| 2006/0252994 A1 | 11/2006 | Ratnakar |
| 2006/0264704 A1 | 11/2006 | Fujimori |
| 2006/0293556 A1 | 12/2006 | Garner |
| 2006/0293562 A1 | 12/2006 | Uchimura |
| 2007/0015964 A1 | 1/2007 | Eversull |
| 2007/0015968 A1 | 1/2007 | Shelnutt |
| 2007/0019916 A1 | 1/2007 | Takami |
| 2007/0020694 A1 | 1/2007 | Pickford |
| 2007/0030345 A1 | 2/2007 | Amling |
| 2007/0049803 A1 | 3/2007 | Moriyama |
| 2007/0055100 A1 | 3/2007 | Kato |
| 2007/0073109 A1 | 3/2007 | Irion |
| 2007/0078304 A1 | 4/2007 | Shimizu |
| 2007/0083081 A1 | 4/2007 | Schlagenhauf |
| 2007/0100206 A1 | 5/2007 | Lin |
| 2007/0106119 A1 | 5/2007 | Hirata |
| 2007/0115376 A1 | 5/2007 | Igarashi |
| 2007/0118019 A1 | 5/2007 | Mitani |
| 2007/0123748 A1 | 5/2007 | Meglan |
| 2007/0142711 A1 | 6/2007 | Bayer |
| 2007/0162095 A1 | 7/2007 | Kimmel |
| 2007/0167673 A1 | 7/2007 | Enomoto |
| 2007/0167681 A1 | 7/2007 | Gill |
| 2007/0173686 A1 | 7/2007 | Lin |
| 2007/0173687 A1 | 7/2007 | Shima |
| 2007/0177008 A1 | 8/2007 | Bayer |
| 2007/0177009 A1 | 8/2007 | Bayer |
| 2007/0185384 A1 | 8/2007 | Bayer |
| 2007/0197875 A1 | 8/2007 | Osaka |
| 2007/0203396 A1 | 8/2007 | McCutcheon |
| 2007/0206945 A1 | 9/2007 | DeLorme |
| 2007/0208225 A1 | 9/2007 | Czaniera |

(56) References Cited

U.S. PATENT DOCUMENTS

| | | |
|---|---|---|
| 2007/0213590 A1 | 9/2007 | Squicciarini |
| 2007/0213591 A1 | 9/2007 | Aizenfeld |
| 2007/0225556 A1 | 9/2007 | Ortiz |
| 2007/0225565 A1 | 9/2007 | Ogino |
| 2007/0229656 A1 | 10/2007 | Khait |
| 2007/0244353 A1 | 10/2007 | Larsen |
| 2007/0244362 A1 | 10/2007 | El-Hachem |
| 2007/0244366 A1 | 10/2007 | Murata |
| 2007/0246506 A1 | 10/2007 | Hamazaki |
| 2007/0249899 A1 | 10/2007 | Seifert |
| 2007/0265498 A1 | 11/2007 | Ito |
| 2007/0282165 A1 | 12/2007 | Hopkins |
| 2007/0293720 A1 | 12/2007 | Bayer |
| 2008/0009672 A1 | 1/2008 | Krattiger |
| 2008/0021274 A1 | 1/2008 | Bayer |
| 2008/0021281 A1 | 1/2008 | Fujimori |
| 2008/0039689 A1 | 2/2008 | Yoshimitsu |
| 2008/0039693 A1 | 2/2008 | Karasawa |
| 2008/0045797 A1 | 2/2008 | Yasushi |
| 2008/0051628 A1 | 2/2008 | Pecherer |
| 2008/0051629 A1 | 2/2008 | Sugiyama |
| 2008/0051655 A1 | 2/2008 | Sato |
| 2008/0058595 A1 | 3/2008 | Snoke |
| 2008/0058598 A1 | 3/2008 | Ries |
| 2008/0058601 A1 | 3/2008 | Fujimori |
| 2008/0064931 A1 | 3/2008 | Schena |
| 2008/0065127 A1 | 3/2008 | Adams |
| 2008/0071290 A1 | 3/2008 | Larkin |
| 2008/0100699 A1 | 5/2008 | Hibi |
| 2008/0108869 A1* | 5/2008 | Sanders ............ A61B 1/00103 600/109 |
| 2008/0130108 A1 | 6/2008 | Bayer |
| 2008/0139881 A1 | 6/2008 | Cover |
| 2008/0163652 A1 | 7/2008 | Shatskin |
| 2008/0167529 A1 | 7/2008 | Otawara |
| 2008/0171910 A1 | 7/2008 | Kanazawa |
| 2008/0177139 A1 | 7/2008 | Courtney |
| 2008/0177140 A1 | 7/2008 | Cline |
| 2008/0188715 A1 | 8/2008 | Fujimoto |
| 2008/0225134 A1 | 9/2008 | Amling |
| 2008/0250637 A1* | 10/2008 | Zhang ................. H05K 3/4635 29/852 |
| 2008/0255425 A1 | 10/2008 | Voegele |
| 2008/0262302 A1 | 10/2008 | Azarbarzin |
| 2008/0262312 A1 | 10/2008 | Carroll |
| 2008/0312497 A1 | 12/2008 | Elmouelhi |
| 2009/0005643 A1 | 1/2009 | Smith |
| 2009/0054790 A1 | 2/2009 | Czaniera |
| 2009/0062615 A1 | 3/2009 | Yamaya |
| 2009/0086017 A1 | 4/2009 | Miyano |
| 2009/0093679 A1 | 4/2009 | Suigetsu |
| 2009/0118577 A9 | 5/2009 | Snay |
| 2009/0137869 A1 | 5/2009 | Soutorine |
| 2009/0147076 A1 | 6/2009 | Ertas |
| 2009/0161234 A1 | 6/2009 | Sasamoto |
| 2009/0163769 A1 | 6/2009 | Robertson |
| 2009/0209811 A1 | 8/2009 | Higuchi |
| 2009/0216084 A1 | 8/2009 | Yamane |
| 2009/0231419 A1 | 9/2009 | Bayer |
| 2009/0247831 A1 | 10/2009 | Miyamoto |
| 2009/0253966 A1 | 10/2009 | Ichimura |
| 2009/0259097 A1 | 10/2009 | Thompson |
| 2009/0259102 A1 | 10/2009 | Koninckx |
| 2009/0268011 A1 | 10/2009 | Scott |
| 2009/0284649 A1 | 11/2009 | Pease |
| 2009/0287047 A1 | 11/2009 | Onoda |
| 2009/0287192 A1 | 11/2009 | Vivenzio |
| 2009/0290236 A1 | 11/2009 | Wang |
| 2009/0299144 A1 | 12/2009 | Shigemori |
| 2009/0306474 A1 | 12/2009 | Wilson |
| 2009/0306476 A1 | 12/2009 | Banik |
| 2009/0318757 A1 | 12/2009 | Singh |
| 2010/0010301 A1 | 1/2010 | Hale |
| 2010/0010302 A1 | 1/2010 | Hadani |
| 2010/0013914 A1 | 1/2010 | Bettesh |
| 2010/0016673 A1 | 1/2010 | Bandy |
| 2010/0030020 A1 | 2/2010 | Sanders |
| 2010/0042097 A1 | 2/2010 | Newton |
| 2010/0047733 A1 | 2/2010 | Nahlieli |
| 2010/0053312 A1 | 3/2010 | Watanabe |
| 2010/0073470 A1 | 3/2010 | Takasaki |
| 2010/0076268 A1 | 3/2010 | Takasugi |
| 2010/0081874 A1 | 4/2010 | Miyamoto |
| 2010/0081875 A1 | 4/2010 | Fowler |
| 2010/0087706 A1 | 4/2010 | Syed |
| 2010/0121142 A1 | 5/2010 | Ouyang |
| 2010/0123950 A1 | 5/2010 | Fujiwara |
| 2010/0130822 A1 | 5/2010 | Katayama |
| 2010/0137682 A1 | 6/2010 | Doguchi |
| 2010/0137687 A1 | 6/2010 | Schwartz |
| 2010/0141746 A1 | 6/2010 | Ikeda |
| 2010/0152612 A1 | 6/2010 | Headley |
| 2010/0160729 A1 | 6/2010 | Smith |
| 2010/0174144 A1 | 7/2010 | Hsu |
| 2010/0185056 A1 | 7/2010 | Gordon |
| 2010/0187408 A1 | 7/2010 | Klem |
| 2010/0201985 A1 | 8/2010 | Wang |
| 2010/0204609 A1 | 8/2010 | Worth |
| 2010/0217076 A1 | 8/2010 | Ratnakar |
| 2010/0217081 A1 | 8/2010 | Deppmeier |
| 2010/0228086 A1 | 9/2010 | Ohki |
| 2010/0245653 A1 | 9/2010 | Bodor |
| 2010/0249496 A1 | 9/2010 | Cardenas |
| 2010/0249513 A1 | 9/2010 | Tydlaska |
| 2010/0256447 A1 | 10/2010 | Dubi |
| 2010/0286475 A1 | 11/2010 | Robertson |
| 2010/0296178 A1 | 11/2010 | Genet |
| 2010/0298640 A1 | 11/2010 | Oneda |
| 2010/0298773 A1 | 11/2010 | Nitsan |
| 2010/0305503 A1 | 12/2010 | Fang |
| 2010/0317919 A1 | 12/2010 | Takaoka |
| 2010/0317921 A1 | 12/2010 | Marple |
| 2010/0318061 A1 | 12/2010 | Derrick |
| 2010/0326703 A1* | 12/2010 | Gilad ...................... A61B 1/041 174/254 |
| 2011/0028790 A1 | 2/2011 | Farr |
| 2011/0054256 A1 | 3/2011 | Cushner |
| 2011/0112363 A1 | 5/2011 | Koga |
| 2011/0118549 A1* | 5/2011 | Han .......................... A61B 1/04 600/109 |
| 2011/0160530 A1 | 6/2011 | Ratnakar |
| 2011/0169931 A1 | 7/2011 | Pascal |
| 2011/0184243 A1 | 7/2011 | Wright |
| 2011/0196200 A1 | 8/2011 | Glozman |
| 2011/0196204 A1 | 8/2011 | Setty |
| 2011/0211267 A1 | 9/2011 | Takato |
| 2011/0224487 A1 | 9/2011 | Ogawa |
| 2011/0245600 A1 | 10/2011 | Ishii |
| 2011/0245609 A1 | 10/2011 | Laser |
| 2011/0257478 A1 | 10/2011 | Kleiner |
| 2011/0263938 A1 | 10/2011 | Levy |
| 2011/0282144 A1 | 11/2011 | Gettman |
| 2011/0282148 A1 | 11/2011 | Kase |
| 2011/0288374 A1 | 11/2011 | Hadani |
| 2011/0295061 A1 | 12/2011 | Haramaty |
| 2011/0295062 A1 | 12/2011 | GratacosSolsona |
| 2011/0295064 A1 | 12/2011 | Kagawa |
| 2011/0306832 A1 | 12/2011 | Bassan |
| 2011/0313249 A1 | 12/2011 | Viola |
| 2012/0010465 A1 | 1/2012 | Erikawa |
| 2012/0029291 A1 | 2/2012 | Wallace |
| 2012/0040305 A1 | 2/2012 | Karazivan |
| 2012/0041534 A1 | 2/2012 | Clerc |
| 2012/0046524 A1 | 2/2012 | Miyamoto |
| 2012/0053407 A1 | 3/2012 | Levy |
| 2012/0057251 A1 | 3/2012 | Takato |
| 2012/0065468 A1 | 3/2012 | Levy |
| 2012/0071748 A1 | 3/2012 | Mark |
| 2012/0078042 A1 | 3/2012 | Uram |
| 2012/0088985 A1 | 4/2012 | Stokes |
| 2012/0095391 A1 | 4/2012 | Bendele |
| 2012/0104230 A1 | 5/2012 | Eismann |
| 2012/0178995 A1 | 7/2012 | Newton |
| 2012/0209062 A1 | 8/2012 | Qiao |

(56) References Cited

U.S. PATENT DOCUMENTS

| | | |
|---|---|---|
| 2012/0229615 A1 | 9/2012 | Kirma |
| 2012/0232340 A1 | 9/2012 | Levy |
| 2012/0232342 A1 | 9/2012 | Reydel |
| 2012/0232343 A1 | 9/2012 | Levy |
| 2012/0253121 A1 | 10/2012 | Kitano |
| 2012/0253284 A1 | 10/2012 | Nitsan |
| 2012/0259175 A1 | 10/2012 | Reydel |
| 2012/0265094 A1 | 10/2012 | Goldfarb |
| 2013/0012778 A1 | 1/2013 | Bayer |
| 2013/0012794 A1 | 1/2013 | Zeng |
| 2013/0060086 A1 | 3/2013 | Talbert |
| 2013/0109916 A1* | 5/2013 | Levy ............. A61B 1/00096 600/109 |
| 2013/0109918 A1 | 5/2013 | Pagan |
| 2013/0110003 A1 | 5/2013 | Surti |
| 2013/0131445 A1 | 5/2013 | Zerfas |
| 2013/0131447 A1 | 5/2013 | Benning |
| 2013/0131454 A1 | 5/2013 | McCormack |
| 2013/0137930 A1 | 5/2013 | Menabde |
| 2013/0172670 A1 | 7/2013 | Levy |
| 2013/0172673 A1 | 7/2013 | Kennedy |
| 2013/0172674 A1 | 7/2013 | Kennedy |
| 2013/0172677 A1 | 7/2013 | Kennedy |
| 2013/0172678 A1 | 7/2013 | Kennedy |
| 2013/0190561 A1 | 7/2013 | Oskin |
| 2013/0194404 A1 | 8/2013 | Christiansen |
| 2013/0204088 A1 | 8/2013 | Miyamoto |
| 2013/0253272 A1 | 9/2013 | Takahashi |
| 2013/0267778 A1 | 10/2013 | Rehe |
| 2013/0296649 A1 | 11/2013 | Kirma |
| 2013/0314521 A1 | 11/2013 | Satake |
| 2013/0317295 A1 | 11/2013 | Morse |
| 2014/0364691 A1 | 12/2014 | Krivopisk |

FOREIGN PATENT DOCUMENTS

| | | |
|---|---|---|
| CN | 1988841 | 6/2007 |
| CN | 2936129 Y | 8/2007 |
| CN | 101061940 A | 10/2007 |
| CN | 201108422 Y | 9/2008 |
| CN | 101386533 A | 3/2009 |
| CN | 101396258 | 4/2009 |
| CN | 101926171 | 12/2010 |
| CN | 102058375 A | 5/2011 |
| CN | 102058380 A | 5/2011 |
| CN | 101061940 | 6/2011 |
| CN | 201870615 U | 6/2011 |
| CN | 102469924 | 5/2012 |
| DE | 102005008153 A1 | 11/2005 |
| EP | 0029555 A2 | 6/1981 |
| EP | 543738 A1 | 5/1993 |
| EP | 8122000657 | 5/1996 |
| EP | 730844 | 9/1996 |
| EP | 1195630 A2 | 4/2002 |
| EP | 1325458 | 7/2003 |
| EP | 1347702 A2 | 10/2003 |
| EP | 948283 B1 | 4/2004 |
| EP | 1535565 | 6/2005 |
| EP | 1073365 B1 | 7/2005 |
| EP | 1627595 A1 | 2/2006 |
| EP | 668738 B1 | 6/2006 |
| EP | 1685790 | 8/2006 |
| EP | 1472972 B1 | 10/2006 |
| EP | 1790280 A1 | 5/2007 |
| EP | 1834572 A1 | 9/2007 |
| EP | 1952750 | 8/2008 |
| EP | 1977675 | 10/2008 |
| EP | 1977682 A2 | 10/2008 |
| EP | 1974000653 | 10/2008 |
| EP | 1992292 A1 | 11/2008 |
| EP | 2022389 A1 | 2/2009 |
| EP | 2144571 A2 | 1/2010 |
| EP | 2276389 A1 | 1/2011 |
| EP | 1835847 B1 | 5/2011 |
| EP | 1870014 B1 | 1/2012 |
| EP | 2501271 A1 | 9/2012 |
| EP | 2503933 A1 | 10/2012 |
| EP | 2512577 A2 | 10/2012 |
| EP | 2529660 A1 | 12/2012 |
| EP | 2596756 A1 | 5/2013 |
| EP | 2623019 A1 | 8/2013 |
| GB | 2321132 | 7/1998 |
| GB | 2352922 A | 2/2001 |
| JP | 85551270 | 5/1980 |
| JP | 55078932 | 6/1980 |
| JP | 61055657 | 11/1986 |
| JP | S6296616 | 6/1987 |
| JP | 6359332 | 11/1988 |
| JP | H0253701 | 4/1990 |
| JP | H02188709 A | 7/1990 |
| JP | H03116801 | 12/1991 |
| JP | H04341232 | 11/1992 |
| JP | 5049000594 | 3/1993 |
| JP | H05309069 | 11/1993 |
| JP | 6105000800 | 4/1994 |
| JP | 7000000352 | 1/1995 |
| JP | 3765500 | 7/1995 |
| JP | 1013007179 | 4/1998 |
| JP | 1015001113 | 6/1998 |
| JP | 11125773 | 5/1999 |
| JP | 11137512 | 5/1999 |
| JP | H11125773 | 5/1999 |
| JP | H11125773 A | 5/1999 |
| JP | 1116009340 | 6/1999 |
| JP | 1116009341 | 6/1999 |
| JP | H11253401 | 9/1999 |
| JP | 2000171727 A | 6/2000 |
| JP | 2000325306 | 11/2000 |
| JP | 2000330015 A | 11/2000 |
| JP | 2001061762 | 3/2001 |
| JP | 2001198086 | 7/2001 |
| JP | 2002000559 | 1/2002 |
| JP | 2002017667 | 1/2002 |
| JP | 2002058636 | 2/2002 |
| JP | 200265589 A | 3/2002 |
| JP | 2002065575 | 3/2002 |
| JP | 2002078675 | 3/2002 |
| JP | 2002216902 | 8/2002 |
| JP | 2002291693 | 10/2002 |
| JP | 2003038431 | 2/2003 |
| JP | 2003061900 | 3/2003 |
| JP | 2003111724 | 4/2003 |
| JP | 2003190082 | 7/2003 |
| JP | 2003220017 | 8/2003 |
| JP | 2003245247 | 9/2003 |
| JP | 2004022391 | 1/2004 |
| JP | 2004049754 | 2/2004 |
| JP | 2004049756 | 2/2004 |
| JP | 2004129834 | 4/2004 |
| JP | 2004205779 A | 7/2004 |
| JP | 200434888 A | 12/2004 |
| JP | 2005013557 A | 1/2005 |
| JP | 2005058547 | 3/2005 |
| JP | 2005253543 | 9/2005 |
| JP | 2005323874 A | 11/2005 |
| JP | 2006003549 A | 1/2006 |
| JP | 2006068109 | 3/2006 |
| JP | 2006068109 A | 3/2006 |
| JP | 2006218155 | 8/2006 |
| JP | 2006280954 | 10/2006 |
| JP | 2006288758 | 10/2006 |
| JP | 2007020866 A | 2/2007 |
| JP | 2007185276 | 7/2007 |
| JP | 2008068025 | 3/2008 |
| JP | 2008118566 | 5/2008 |
| JP | 2008073243 | 6/2008 |
| JP | 2008161569 A | 7/2008 |
| JP | 2008229204 | 10/2008 |
| JP | 2008257108 A | 10/2008 |
| JP | 2009233186 | 10/2009 |
| JP | 2009251574 | 10/2009 |
| JP | 4445647 | 4/2010 |
| JP | 2010178766 A | 8/2010 |

(56) References Cited

FOREIGN PATENT DOCUMENTS

| | | |
|---|---|---|
| JP | 2010279539 | 12/2010 |
| WO | 921948 A1 | 11/1992 |
| WO | 00052643 A1 | 9/2000 |
| WO | 2002045595 | 6/2002 |
| WO | 2004026125 | 4/2004 |
| WO | 2005082228 A1 | 9/2005 |
| WO | 2006073581 | 7/2006 |
| WO | 2006105932 A1 | 10/2006 |
| WO | 2007113801 A2 | 10/2007 |
| WO | 2007087421 | 11/2007 |
| WO | 2007136859 A2 | 11/2007 |
| WO | 2008012813 A1 | 1/2008 |
| WO | 2008093288 | 8/2008 |
| WO | 2008139770 | 11/2008 |
| WO | 2008155776 | 12/2008 |
| WO | 2008156623 | 12/2008 |
| WO | 2009009414 | 1/2009 |
| WO | 2009025843 | 2/2009 |
| WO | 2009040744 | 4/2009 |
| WO | 2009095915 | 8/2009 |
| WO | 2010021342 | 2/2010 |
| WO | 2010028612 | 3/2010 |
| WO | 2010045406 | 4/2010 |
| WO | 2010064506 | 6/2010 |
| WO | 2010066788 | 6/2010 |
| WO | 2010146587 | 12/2010 |
| WO | 2010146587 A1 | 12/2010 |
| WO | 20100146587 | 12/2010 |
| WO | 2011008922 | 1/2011 |
| WO | 2011041724 | 4/2011 |
| WO | 2011083451 | 7/2011 |
| WO | 2011126812 | 10/2011 |
| WO | 2012038958 | 3/2012 |
| WO | 2012056453 | 5/2012 |
| WO | 2012077116 | 6/2012 |
| WO | 2012077117 | 6/2012 |
| WO | 2012103266 | 8/2012 |
| WO | 2012088201 A2 | 9/2012 |
| WO | 2012120507 | 9/2012 |
| WO | 2012153324 | 11/2012 |
| WO | 2013014673 | 1/2013 |
| WO | 2013024476 | 2/2013 |
| WO | 2013043704 | 3/2013 |
| WO | 2013128136 | 9/2013 |
| WO | 2013131578 | 9/2013 |
| WO | 2013144944 | 10/2013 |
| WO | 2014061023 | 4/2014 |

OTHER PUBLICATIONS

Date verified for NPL document U as Oct. 21, 2006.*
Office Action for Chinese Patent Application No. 201180062736.6, dated Dec. 23, 2016.
Office Action for Japanese Patent Application No. 2018-105009, dated Jan. 16, 2017.
Office Action for Chinese Patent Application No. 201360053351.2, dated Dec. 13, 2016.
First Office Action for EP11847191.1, dated Feb. 21, 2017.
Notice of Allowance dated Apr. 16, 2017 for U.S. Appl. No. 13/713,449.
Examination Report for EP11846069.0, dated Feb. 21, 2017.
Extended European Search Report for EP1182E512.3, dated Apr. 6, 2017.
Office Action dated May 23, 2017 for U.S. Appl. No. 13/655,120.
Notice of Allowance dated Aug. 26, 2016 for U.S. Appl. No. 13/212,627.
Notice of Allowance dated Oct. 12, 2016 for U.S. Appl. No. 13/119,032.
Offfee Action dated Oct. 7, 2015 for U.S. Appl. No. 13/713,449.
Notice of Allowance dated Nov. 9, 2016 for U.S. Appl. No. 13/557,114.
Third Office Action for Chinese Patent Application No. 201180067259.2, dated Oct. 21, 2016.
Extended European Search Report for EP11847191.1, dated Jan. 15, 2016.
Examination Report for Canadian Patent Application No. CA2765559, dated Jan. 18, 2016.
Examination Search Report for Canadian Patent Application No. CA2765559, dated Jan. 18, 2016.
Extended European Search Report for EP11846089.0, dated Apr. 24, 2014.
Extended European Search Report for EP12817452.1, dated Mar. 9, 2015.
First Office Action for Chinese Patent Applicatio No. CN201380053351.2, dated Mar. 2, 2016.
Notice of Allowance dated Dec. 15, 2014 for U.S. Appl. No. 13/713,466.
Notice of Allowance dated Dec. 15, 2015 for U.S. Appl. No. 13/713,456.
Notice of Allowance dated Dec. 23, 2015 for U.S. Appl. No. 13/992,021.
Office Action dated Aug. 27, 2015 for U.S. Appl. No. 13/655,120.
Office Action dated Dec. 4, 2015 for U.S. Appl. No. 13/822,908.
Office Action dated Jan. 12, 2016 for U.S. Appl. No. 13/713,466.
Office Action dated Nov. 16, 2015 for U.S. Appl. No. 13/557,114.
Office Action dated Nov. 24, 2015 for U.S. Appl. No. 13/413,059.
Office Action dated Oct. 7, 2015 for U.S. Appl. No. 13/882,004.
Office Action for Chinese Patent Application No. 201280038808.8, dated May 20, 2015.
Office Action for Japanese Patent Application No. 2013-525586, dated Sep. 24, 2015.
Office Action for Japanese Patent Application No. 2013-542668, dated Oct. 1, 2015.
Second Office Action for Chinese Patent Application No. CN201280038808.8, dated Feb. 25, 2016.
Second office action for Chinese Patent Application No. 201180062736.6, dated Oct. 12, 2015.
Supplementary European Search Report for EP118471911, dated Jan. 16, 2015.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action for Japanese Patent Application No. JP2014-522214, dated Apr. 26, 2016.
Office Action for Japanese Patent Application No. JP2014-525562, dated Apr. 26, 2016.
Second image of an Endo Smart Cap, made by Medivators, and obtained from http://www.bymemedical.com/prod/150L.jpg and advertised at http://www.medivators.com/products/endoscopy-procedure-products/irrigation-tubing/endo-smartcap%C2%AE.
Office Action dated Jun. 30, 2016 for U.S. Appl. No. 13/655,120.
Second Office Action for Chinese Patent Application No. 201180067259.2, dated Mar. 30, 2016.
Extended European Search Report for application No. EP12755186, completed on May 23, 2016.
Supplementary European Search Reoprt for EP13847670, completed on May 19, 2016.
Notice of Allowance dated Jun. 8, 2015 for U.S. Appl. No. 13/984,028.
Notice of Allowance dated Jun. 8, 2015 for U.S. Appl. No. 13/413,252.
Prosecution File History for U.S. Appl. No. 13/190,968; Jul. 26, 2011 through Jun. 17, 2015.
Notice of Allowance dated Jun. 17, 2015 for U.S. Appl. No. 13/190,968.
Supplementary European Search Reoprt for European Application No. EP12823972, dated May 13, 2015.
Extended Europeen Search Report for EP14186113.8, dated Apr. 1, 2015.
Corrected European Search Opinion for EP14188113.8, dated Apr. 29, 2015.
International Search Report for PCT/EP2009/066726, dated Aug. 18, 2010.
Brochure for US Endoscopy's AquaShield Water Bottle System, 2010.
First Image of an Endo Smart Cap, made by Medivators, and obtained from http://www.bymsmedical.com/prod/146L.jpg and adver-

(56) References Cited

OTHER PUBLICATIONS tised at http://www.medivators.com/products/endosocopy-procedure-products/irrigation-tubing/endo-smartcap%C2%AE.
Office Action dated Feb. 27, 2014 for U.S. Appl. No. 13/557,114.
International Search Report of PCT/IL2011/000745, dated May 8, 2012.
International Search Report for PCT/IL2011/000832, dated May 16, 2012.
International Search Report for PCT/IL2011/050049, dated May 15, 2012.
International Search Report for PCT/IL2011/050050, dated May 16, 2012.
International Search Report for PCT/IL2012/050037, dated Jun. 1, 2012.
International Search Report for PCT/IL2012/050274, dated Nov. 15, 2012.
International Search Report for PCT/IL2012/050299, dated Nov. 15, 2012.
International Search Report for PCT/IL2013/050840, dated Feb. 2, 2014.
International Search Report for PCT/IL10/00476 dated Sep. 27, 2010, 2 pages.
Office Action dated Apr. 3, 2014 for U.S. Appl. No. 13/413,141.
Office Action dated Feb. 24, 2014 for U.S. Appl. No. 13/190,968.
Office Action dated Jul. 1, 2014 for U.S. Appl. No. 13/655,120.
Office Action dated Jul. 31, 2014 for U.S. Appl. No. 13/713,449.
Office Action dated Jun. 12, 2014 for U.S. Appl. No. 13/713,466.
Office Action dated Mar. 28, 2014 for U.S. Appl. No. 13/413,252.
Office Action dated May 27, 2014 for U.S. Appl. No. 13/212,627.
Office Action dated May 30, 2014 for U.S. Appl. No. 13/119,032.
Office Action dated May 9, 2014 for U.S. Appl. No. 13/413,059.

\* cited by examiner

FLEXIBLE ELECTRONIC CIRCUIT BOARD FOR A MULTI CAMERA ENDOSCOPE

CROSS REFERENCE

This application is a continuation of U.S. patent application Ser. No. 13/992,014, filed on Jun. 6, 2013, which is the U.S. National Stage entry under 35 U.S.C. § 371 of PCT/IL2011/050049, filed on Dec. 8, 2011, which claims the benefit of priority of U.S. Provisional Application No. 61/421,238, filed on Dec. 9, 2010, each of which is incorporated by reference herein in its entirety.

FIELD

Embodiments of the disclosure relate to a multi-camera endoscope having a flexible electronic circuit board.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

Endoscopes, such as colonoscopes, that are currently being used, typically have a front camera for viewing the internal organ, such as the colon, an illuminator, a fluid injector for cleaning the camera lens and sometimes also the illuminator and a working channel for insertion of surgical tools, for example, for removing polyps found in the colon. Often, endoscopes also have fluid injectors ("jet") for cleaning a body cavity, such as the colon, into which they are inserted. The illuminators commonly used are fiber optics which transmit light, generated remotely, to the endoscope tip section. The use of light-emitting diodes (LEDs) for illumination is also known.

Among the disadvantages of such endoscopes, are their limited field of view and their complicated packing of all the required elements, such as electronics and fiber optics together with fluid carrying elements in the small sized endoscope tip section.

There is thus a need in the art for endoscopes, such as colonoscopies, that allow a broader field of view and also enable the efficient packing of all necessary elements in the tip section, while maintaining their function.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

According to some embodiments, there is provided a flexible electronic circuit board for a tip section of a multi-camera endoscope, the circuit board comprising: a front camera surface configured to carry a forward looking camera; a first side camera surface configured to carry a first side looking camera; a second side camera surface configured to carry a second side looking camera; one or more front illuminator surfaces configured to carry one or more front illuminators to essentially illuminate the Field Of View (FOV) of the forward looking camera; one or more side illuminator surfaces configured to carry one or more side illuminators to essentially illuminate the FOV of the first side looking camera; and one or more side illuminator surfaces configured to carry one or more side illuminators to essentially illuminate the FOV of the second side looking camera. The term "essentially illuminate the FOV of" may also refer to illuminating only a part of the FOV. The one or more front illuminator surfaces may include three front illuminator surfaces.

The front camera surface and said one or more front illuminator surfaces may be essentially parallel to each other, and essentially perpendicular to a center portion of said flexible electronic circuit board, when said flexible electronic circuit board is in a folded configuration.

According to some embodiments, when said flexible electronic circuit board is in a folded configuration, said first side camera surface and said second side camera surface are essentially parallel to each other, such that said first side looking camera and said second side looking camera are directed to opposing sides.

According to some embodiments, when said flexible electronic circuit board is in a folded configuration, said first side camera surface and said second side camera surface are essentially perpendicular to a center portion of said flexible electronic circuit board.

According to some embodiments, when said flexible electronic circuit board is in a folded configuration, said first side camera surface and said second side camera surface are essentially perpendicular to said front camera surface.

According to some embodiments, said one or more side illuminator surfaces comprises two side illuminator surfaces.

According to some embodiments, said two side illuminator surfaces are configured to carry two side illuminators to essentially illuminate the FOV of the first side looking camera, and wherein, when said flexible electronic circuit board is in a folded configuration, said two side illuminator surfaces are essentially parallel to each other and essentially perpendicular to said first side camera surface, which is located between them.

According to some embodiments, said two side illuminator surfaces are configured to carry two side illuminators to essentially illuminate the FOV of the second side looking camera, and wherein, when said flexible electronic circuit board is in a folded configuration, said two side illuminator surfaces are essentially parallel to each other and essentially perpendicular to said second side camera surface, which is located between them.

According to some embodiments, there is provided a tip section of a multi-camera endoscope, the tip section comprising: a folded flexible electronic circuit board for a tip section of a multi-camera endoscope, the circuit board comprising: a front camera surface configured to carry a forward looking camera; a first side camera surface configured to carry a first side looking camera; a second side camera surface configured to carry a second side looking camera; one or more front illuminator surfaces a configured to carry one or more front illuminators to essentially illuminate the FOV of the forward looking camera; one or more side illuminator surfaces configured to carry one or more side illuminators to essentially illuminate the FOV of the first side looking camera; and one or more side illuminator surfaces configured to carry one or more side illuminators to essentially illuminate the FOV of the second side looking camera; and a flexible electronic circuit board holder configured to retain said flexible electronic circuit board in a folded position.

According to some embodiments, the tip section of an endoscope (such as a colonoscope) is the most distal part of the endoscope which terminates the endoscope. The tip section is turnable by way of a bending section connected thereto.

According to some embodiments, the tip section further includes a fluid channeling component adapted to channel fluid for insufflations and/or irrigation. The fluid channeling component may be a unitary component comprising a front fluid channel leading to a front opening at a distal end of said unitary fluid channeling component, for cleaning one or more front optical elements of said tip section, and a side fluid channel leading to a left side opening and to a right side opening in said unitary fluid channeling component, for cleaning side optical elements of said tip section. The unitary fluid channeling component may further include a working channel adapted for the insertion of a medical tool. The unitary fluid channeling component may further include a jet fluid channel adapted to clean a body cavity into which said endoscope is inserted.

According to some embodiments, the one or more front illuminator surfaces comprises three front illuminator surfaces.

According to some embodiments, said front camera surface and said one or more front illuminator surfaces are essentially parallel to each other, and essentially perpendicular to a center portion of said flexible electronic circuit board.

According to some embodiments, said first side camera surface and said second side camera surface are essentially parallel to each other, such that said first side looking camera and said second side looking camera are directed to opposing sides. According to some embodiments, said first side camera surface and said second side camera surface are essentially perpendicular to a center portion of said flexible electronic circuit board. According to some embodiments, said first side camera surface and said second side camera surface are essentially perpendicular to said front camera surface.

According to some embodiments, said one or more side illuminator surfaces comprises two side illuminator surfaces. According to some embodiments, said two side illuminator surfaces are configured to carry two side illuminators to essentially illuminate the FOV of the first side looking camera, and wherein, when said flexible electronic circuit board is in a folded configuration, said two side illuminator surfaces are essentially parallel to each other and essentially perpendicular to said first side camera surface, which is located between them.

According to some embodiments, said two side illuminator surfaces are configured to carry two side illuminators to essentially illuminate the FOV of the second side looking camera, and wherein, when said flexible electronic circuit board is in a folded configuration, said two side illuminator surfaces are essentially parallel to each other and essentially perpendicular to said second side camera surface, which is located between them.

According to some embodiments, the flexible electronic circuit board holder may be configured to be used as a heat sink for one or more of the side and front illuminators.

According to some embodiments, the tip section has having a diameter of about 17 mm or less. According to some embodiments, the tip section has having a diameter of about 12 mm or less. According to some embodiments, the tip section has having a diameter of about 10 mm or less.

According to some embodiments, there is provided herein a multi-camera endoscope, such as a colonoscope, comprising the tip section disclosed herein. According to some embodiments, the tip section of an endoscope (such a colonoscope) is the most distal part of the endoscope which terminates the endoscope. The tip section is turnable by way of a bending section connected thereto.

More details and features of the current invention and its embodiments may be found in the description and the attached drawings.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

Figure 1:
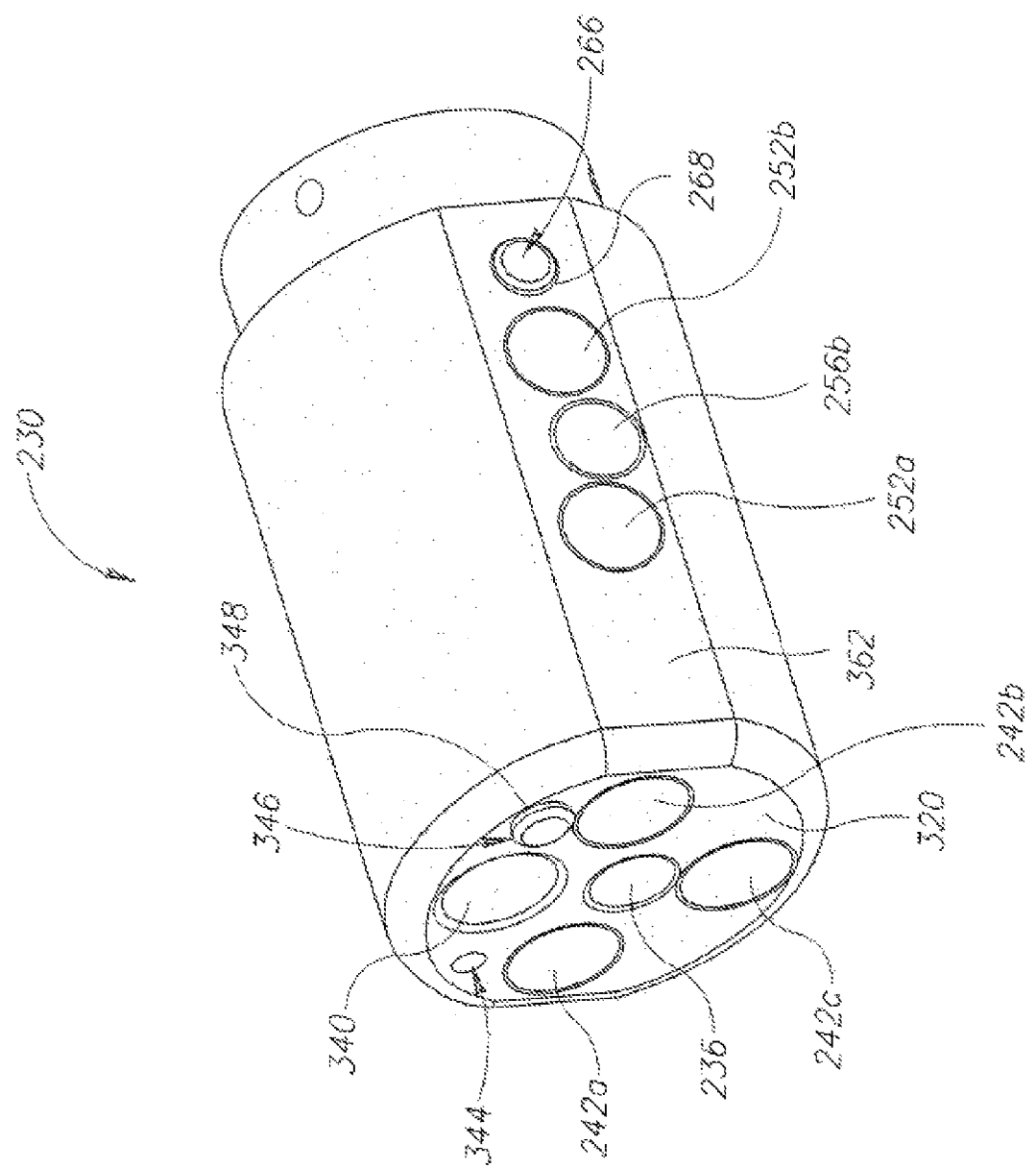
FIG. 1 schematically depicts an external isometric view of a tip section of an endoscope having multiple fields of view, according to an exemplary embodiment of the current invention.

FIG. 1 schematically depicts an external isometric view of a tip section of an endoscope having multiple fields of view according to an exemplary embodiment of the current invention.

According to an exemplary embodiment of the current invention, tip section 230 of an endoscope which comprises at least a forwards looking camera and at least one side looking camera. Tip section 230 is turnable by way of flexible shaft (not shown) which may also be referred to as a bending section, for example a vertebra mechanism).

In some embodiments, the front-looking camera and/or any of the side-looking cameras comprises a Charge Coupled Device (CCD) or a Complementary Metal Oxide Semiconductor (CMOS) image sensor.

It is noted that the term "endoscope" as mentioned to herein may refer particularly to a colonoscope, according to some embodiments, but is not limited only to colonoscopes. The term "endoscope" may refer to any instrument used to examine the interior of a hollow organ or cavity of the body.

Tip section 230 includes front optical assembly 236 of forwards looking camera 116 (seen for example in FIGS. 2 and 5-8) on the front face 320 of tip section 230. Optical axis of forwards looking camera 116 is substantially directed along the long dimension of the endoscope. However, since forward looking camera 116 is typically a wide angle camera, its Field Of View (FOV) may include viewing directions at large angles to its optical axis. Additionally, optical windows 242a, 242b and 242c of LEDs 240a, 240b and 240c, respectively, (seen for example in FIGS. 2 and 5-8) are also located on front face 320 of tip section 230. It should be noted that number of illumination sources such as LEDs used for illumination of the FOV may vary (for example, 1-5 LEDs may be used on front face 320 of tip section 230). Distal opening 340 of a working channel (not shown) is also located on front face 320 of tip section 230, such that a surgical tool inserted through working channel tube, and through the working channel in the endoscope's tip section 230 and deployed beyond front face 320 may be viewed by forwards looking camera 116.

Distal opening 344 of a jet fluid channel is also located on front face 320 of tip section 230. Distal opening 344 of a jet fluid channel may be used for providing high pressure jet of fluid such as water or saline for cleaning the walls of the body cavity.

Also located on front face 320 of tip section 230 is an irrigation and insufflation (I/I) injector 346 having a nozzle 348 aimed at front optical assembly 236. I/I injector 346 may be used for injecting fluid (liquid and/or gas) to wash contaminants such as blood, feces and other debris from front optical assembly 236 of forwards looking camera. Optionally the same injector is used for cleaning front optical assembly 236 and one two or all of optical windows 242a, 242b and 242c. I/I injector 346 may be fed by fluid such as water and/or gas which may be used for cleaning and/or inflating a body cavity.

Visible on the side wall 362 of tip section 230 is the side camera (side looking camera) element 256b of side looking camera 220b and optical windows 252a and 252b of LEDs 250a and 250b for camera 220b. A second side looking camera, 220a, is not shown in FIG. 1 but can be seen for example in FIGS. 2 and 5-6, along with its optical assemblies 256a and optical windows 252a' and 252b' of LEDs 250a' and 250b' of camera 220a. Optical axis of side looking camera 220a is substantially directed perpendicular to the long dimension of the endoscope. Optical axis of side looking camera 220b is substantially directed perpendicular to the long dimension of the endoscope. However, since side looking cameras 220a and 220b is typically a wide angle camera, its field of view may include viewing directions at large angles to its optical axis.

I/I injector 266 having a nozzle 268 aimed at side optical assembly 256b may be used for injecting fluid to wash contaminants such as blood, feces and other debris from side optical assembly 256b of side looking camera. The fluid may include gas which may be used for inflating a body cavity. Optionally the same injector is used for cleaning both side optical assembly 256b and optical windows 252a and/or 252b. It is noted that according to some embodiments, the tip may include more than one window and LEDs, on the side and more than one window and LEDs in the front (for example, 1-5 windows and two LEDs on the side). Similar configuration of I/I injector and nozzle exists for cleaning optical assembly 256a and optical windows 252a' and 252b' located on the other side of tip 230. The I/I injectors are configured to clean all or a part of these windows/LEDs. I/I injectors 346 and 266 may be fed from same channel.

It is noted that the side wall 362 has a form of an essentially flat surface which assists in directing the cleaning fluid injected from I/I injector 266 towards side optical assembly 256b and optical windows 252a and/or 252b. Lack of such flat surface may result in dripping of the cleaning fluid along the curved surface of tip section 230 of the endoscope without performing the desired cleaning action.

It should be noted that while only one side looking camera is seen in FIG. 1, preferably at least two side looking cameras may be located within tip section 230. When two side looking cameras are used, the side looking cameras are preferably installed such that their field of views are substantially opposing. However, different configurations and number of side looking cameras are possible within the general scope of the current invention.

A significant problem always existed in the art when attempts were made to pack all necessary components into the small inner volume of the endoscope. This problem dramatically increases when three cameras and respective illumination sources (such as LEDs) should be packed in the tip of the endoscope, as disclosed herein in accordance to some embodiments of the present invention. There is thus provided, according to some embodiments of the invention, a flexible electronic circuit for carrying and packing within the limited inner volume of the endoscope's tip, at least a front camera and one or more (for example two) side view cameras and their respective illumination sources.

According to some embodiments, the flexible circuit board consumes less space and leaves more volume for additional necessary features. The flexibility of the board adds another dimension in space that can be used for components positioning.

The use of the circuit board according to embodiments of the invention can significantly increase reliability of the electric modules connection thereto as no wires are for components connectivity. In addition, according to some embodiments, the components assembly can be machined and automatic.

The use of the circuit board according to embodiments of the invention, may also allow components (parts) movement and maneuverability during assembly of the camera head (tip of the endoscope) while maintaining high level of reliability. The use of the circuit board according to embodiments of the invention, may also simplify the (tip) assembling process.

According to some embodiments, the flexible circuit board is connected to the control unit via multi wire cable; this cable is welded on the board in a designated location freeing additional space within the tip assembly and adding flexibility to cable access. Assembling the multi wire cable directly to the electrical components was a major challenge which is mitigated by the use of the flexible board according to embodiments of the invention.

Figure 2:
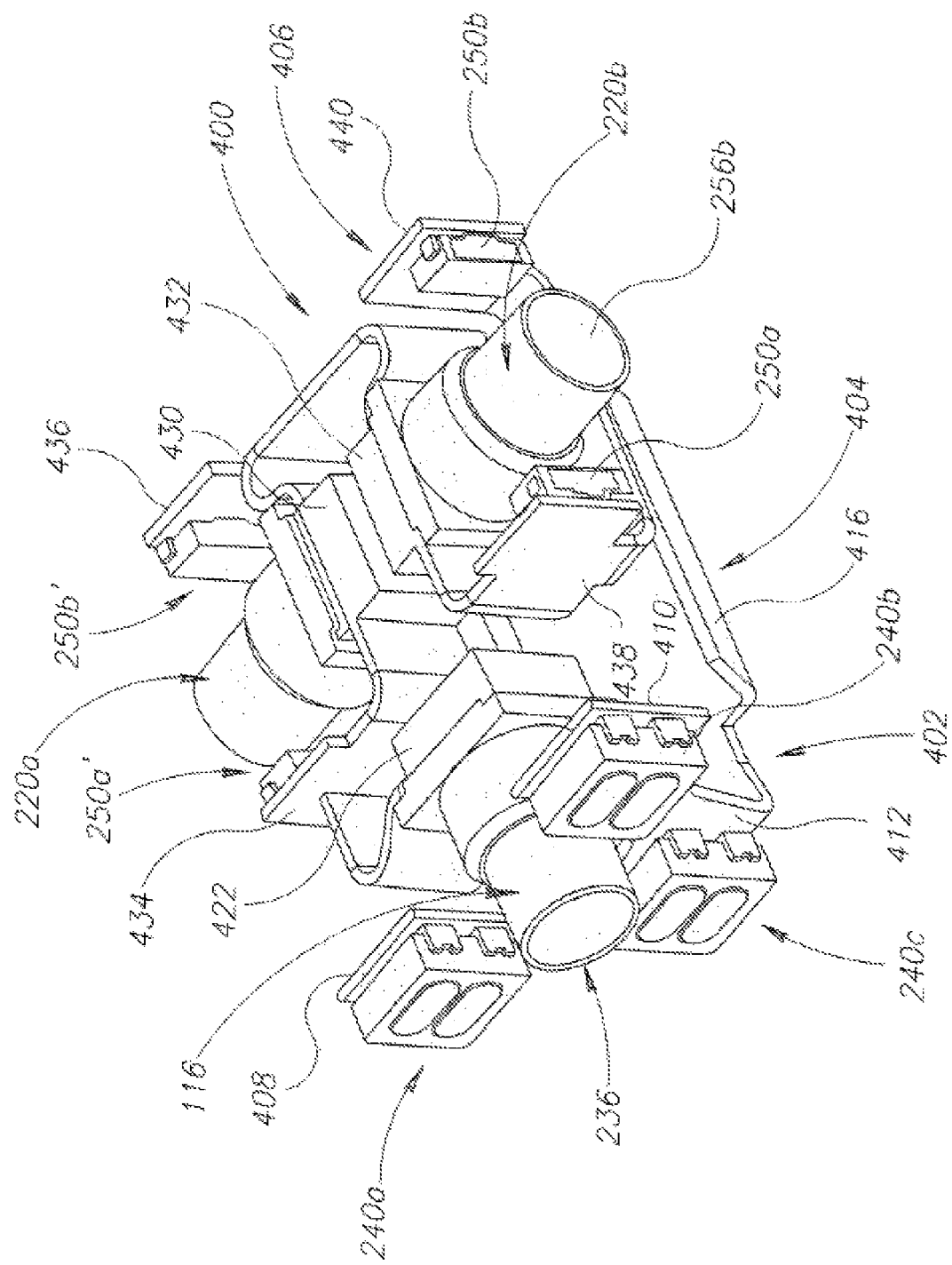
FIG. 2 schematically depicts an isometric view of a folded flexible electronic circuit board carrying a front view camera, two side view cameras and illumination sources, according to an exemplary embodiment of the current invention.

FIG. 2 schematically depicts an isometric view of a folded flexible electronic circuit board carrying a front view camera, two side view cameras and illumination sources, according to embodiments of the invention.

Flexible electronic circuit board 400, shown here in a folded configuration, is configured to carry forward looking camera 116; LEDs 240a, 240b and 240c positioned to essentially illuminate the Field Of View (FOV) of forward looking camera 116; side looking cameras 220b; LEDs 250a and 250b positioned to essentially illuminate the Field Of View (FOV) of side looking cameras 220b; side looking cameras 220a and LEDs 250a' and 250b' positioned to essentially illuminate the Field Of View (FOV) of side looking cameras 220a.

Figure 3:
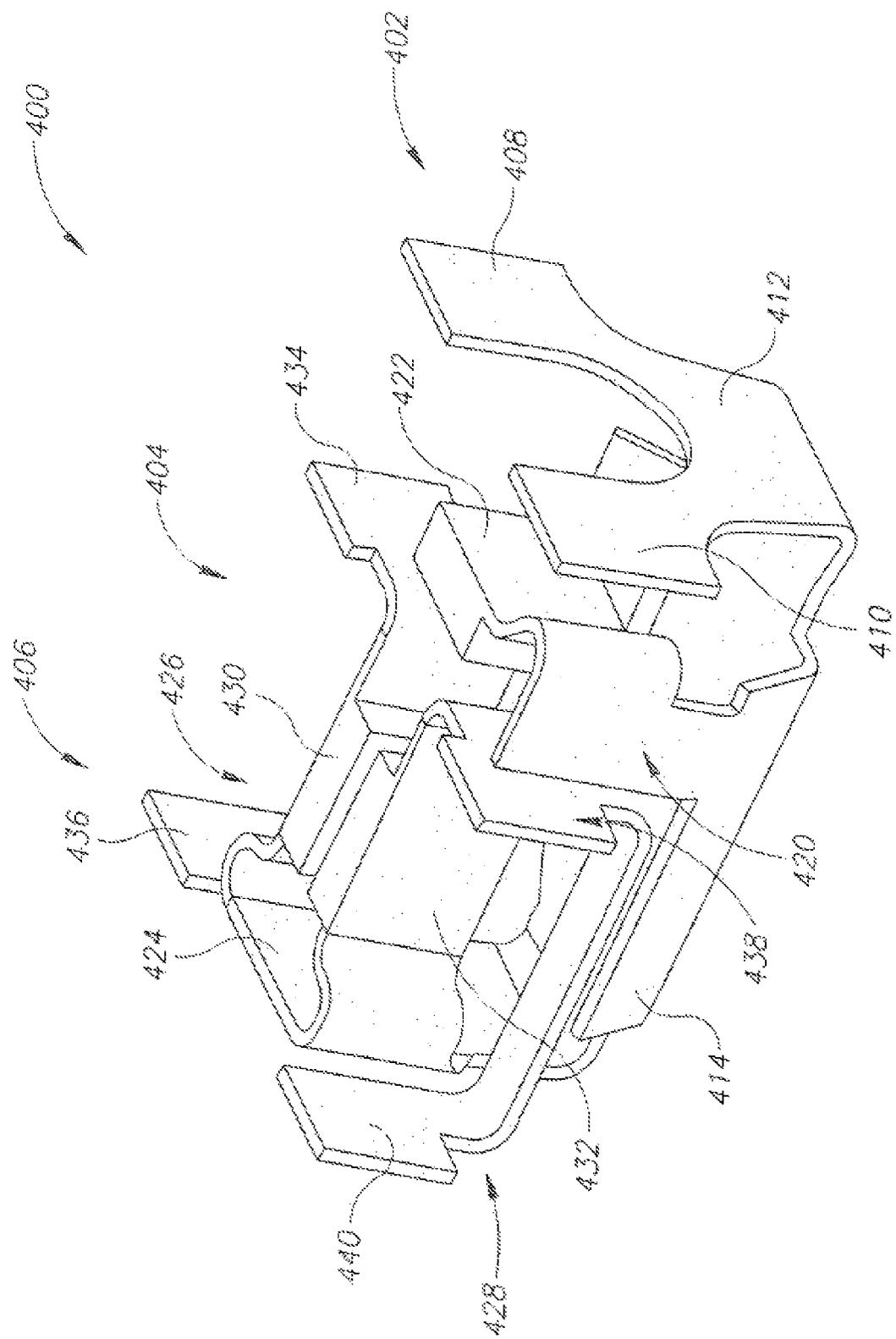
FIG. 3 schematically depicts an isometric view of a folded flexible electronic circuit board, according to an exemplary embodiment of the current invention.
Figure 4:
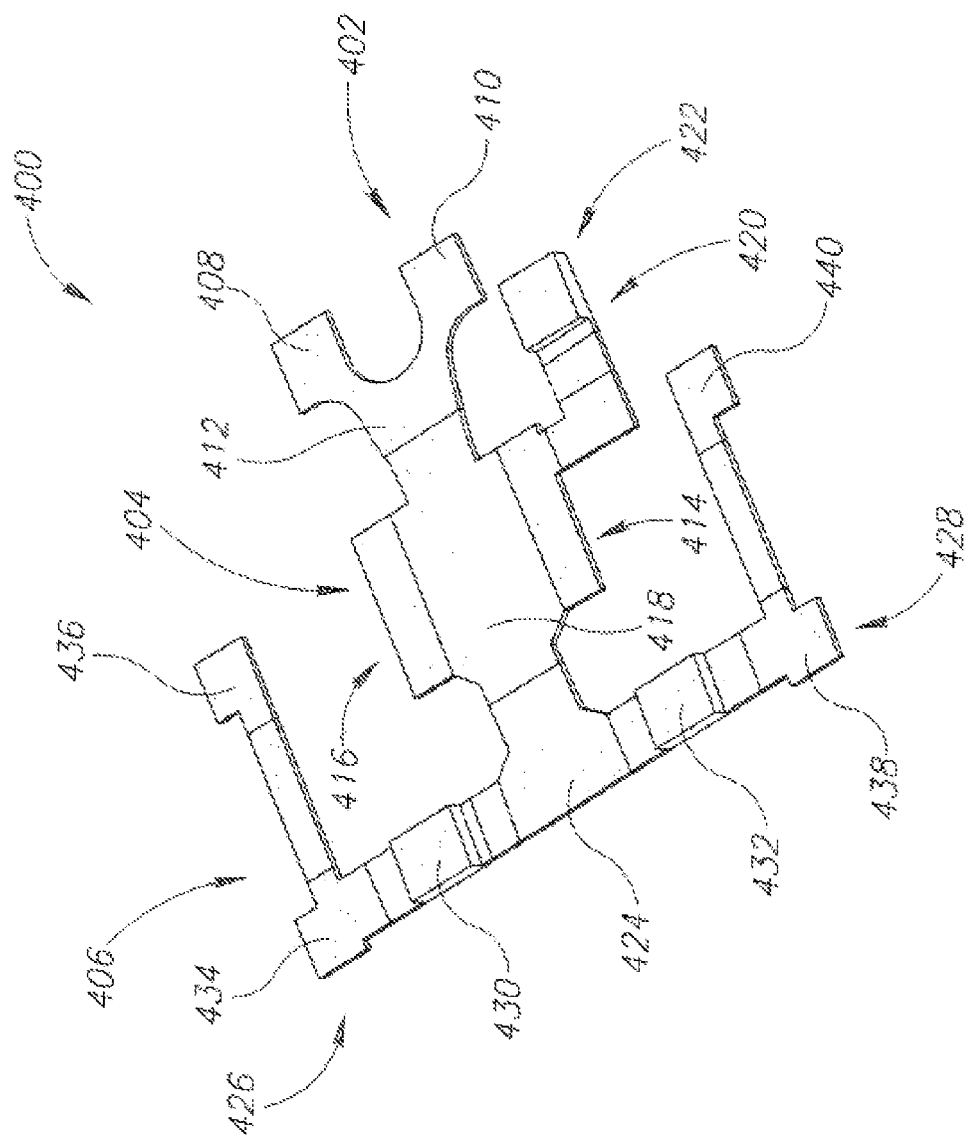
FIG. 4 schematically depicts an isometric view of a flexible electronic circuit board in an unfolded (flat) configuration, according to an exemplary embodiment of the current invention.

As can also be seen in FIGS. 3 and 4, which schematically depict isometric views of flat and folded flexible electronic circuit board, respectively, according to embodiments of the invention, flexible electronic circuit board 400 includes three sections: front section 402, main section 404 and rear section 406.

Front section 402 of flexible electronic circuit board 400 includes first front LED surface 408, second front LED surface 410 and a bottom front LED surface 412. First front LED surface 408, second front LED surface 410 and a bottom front LED surface 412 are flat surfaces formed from a unitary piece of a PCB layer. First front LED surface 408 is adapted to carry front LED 240a, second front LED surface 410 is adapted to carry front LED 240b and a bottom front LED surface 412 is adapted to carry front LED 240c. First front LED surface 408, second front LED surface 410 and a bottom front LED surface 412 form an arc shape between them which is configured to support forward looking camera 116.

Front section 402 of flexible electronic circuit board 400 is connected to main section 404 through bottom section 412. Main section 404 of flexible electronic circuit board 400 includes a center potion 418, a first foldable side panel 414 and a second foldable side panel 416. When flexible electronic circuit board 400 is in a folded configuration, first foldable side panel 414 and a second foldable side panel 416 are configured to fold upwards (towards the length axis of the endoscope tip), for example, as shown herein, forming an angle of about 45 degrees with center portion 418 of main section 404. First foldable side panel 414 also includes an arm section 420, extending therefrom, having a front sensor surface 422 (may also be referred to as a camera surface) adapted to carry forward looking camera 116. When flexible electronic circuit board 400 is in folded position, arm section 420 is folded to be essentially perpendicular to center portion 418 of main section 404, and front sensor surface 422 is folded to be essentially perpendicular to center portion 418 and to arm section 420, such that it faces forwards, essentially at the same direction of first front LED surface 408, second front LED surface 410 and a bottom front LED surface 412. This configuration enables forward looking camera 116 and LEDs 240a-c to face the same direction.

As described hereinabove, main section 404 is connected to bottom section 412 of front section 402. On the opposing end of main section 404, it is connected to rear section 406.

Rear section 406 includes a rear central portion 424. Rear central portion 424 is connected to a first rear arm section 426, extending from one side of rear central portion 424 and to a second rear arm section 428, extending from the opposing side of rear central portion 424.

First rear arm section 426 includes a first side sensor surface 430 (adapted to carry side looking camera 220a). Second rear arm section 428 includes a second side sensor surface 432 (adapted to carry side looking camera 220b).

First rear arm section 426 further includes a first side LED surface 434 and a second side LED surface 436, adapted to carry side LEDs 250a' and 250b', respectively. Second rear arm section 428 further includes a third side LED surface 438 and a fourth side LED surface 440, adapted to carry side LEDs 250a and 250b, respectively.

According to some embodiments, front sensor surface 422 (which is adapted carry forward looking camera 116), first side sensor surface 430 and second side sensor surface 432 (which are adapted carry side looking cameras 220a and 220b) are thicker than the front and side LED surfaces. For example, the sensor surface thickness is configured for locating the sensor (of the camera) such that the welding pins of the sensor wrap the surface and are welded on the opposite side of the sensor in specific welding pads.

The sensor surfaces may be rigid and used as basis for the camera assembly. The height of the sensor surface has significant importance allowing the sensor conductors to bend in a way they will directly reach the welding pads on the opposite side of the sensor rigid surface. The rigid basis also serves as electrical ground filtering electromagnetic noise to and from the sensor and thus increasing signal integrity.

When flexible electronic circuit board 400 is in a folded configuration, rear central portion 424 is folded upwards, perpendicularly to center potion 418 of main section 404. First side sensor surface 430 and second side sensor surface 432 are positioned perpendicularly to center potion 418 and also perpendicularly rear central portion 424. In addition, first side sensor surface 430 and second side sensor surface 432 are positioned essentially parallel and "back to back" to each other such that when they carry side looking camera 220a and side looking camera 220b, these cameras view opposing sides. First side LED surface 434 and a second side LED surface 436 are positioned perpendicularly to first side sensor surface 430 and adapted to carry, on their inner sides, side LEDs 250a' and 250b', respectively, such that LEDs 250a' and 250b' are positioned in proximity to side looking camera 220a. Third side LED surface 438 and a fourth side LED surface 440 are positioned perpendicularly to second side sensor surface 432 and adapted to carry, on their inner sides, side LEDs 250a and 250b, respectively, such that LEDs 250a and 250b are positioned in proximity to side looking camera 220b.

According to some embodiments of the invention, front section 402, main section 404 and rear section 406 of flexible electronic circuit board 400 are all integrally formed from a unitary piece of circuit board layer.

Figure 5:
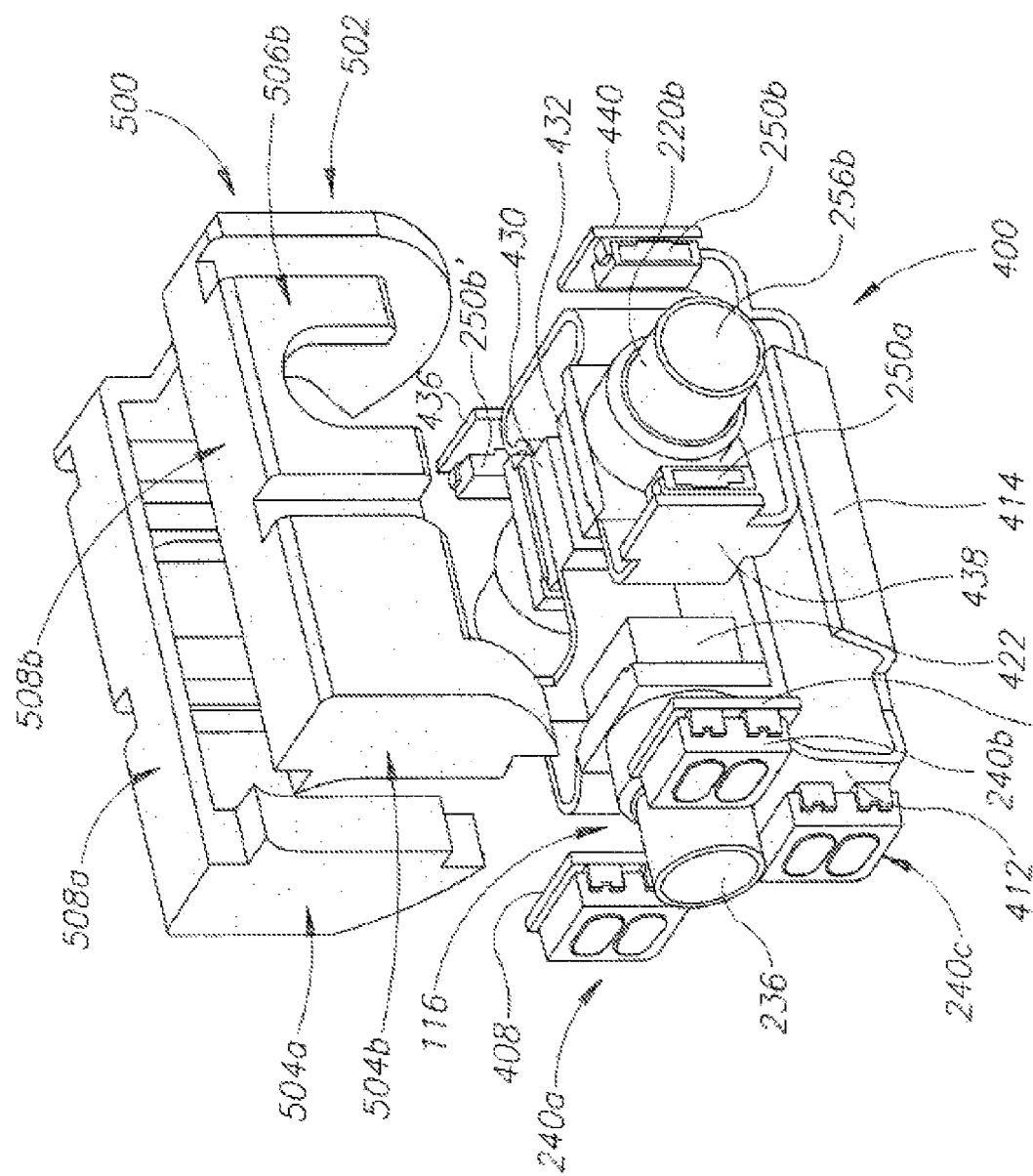
FIG. 5 schematically depicts an isometric exploded view of a folded flexible electronic circuit board carrying cameras and illumination sources and a flexible electronic circuit board holder, according to an exemplary embodiment of the current invention.
Figure 6:
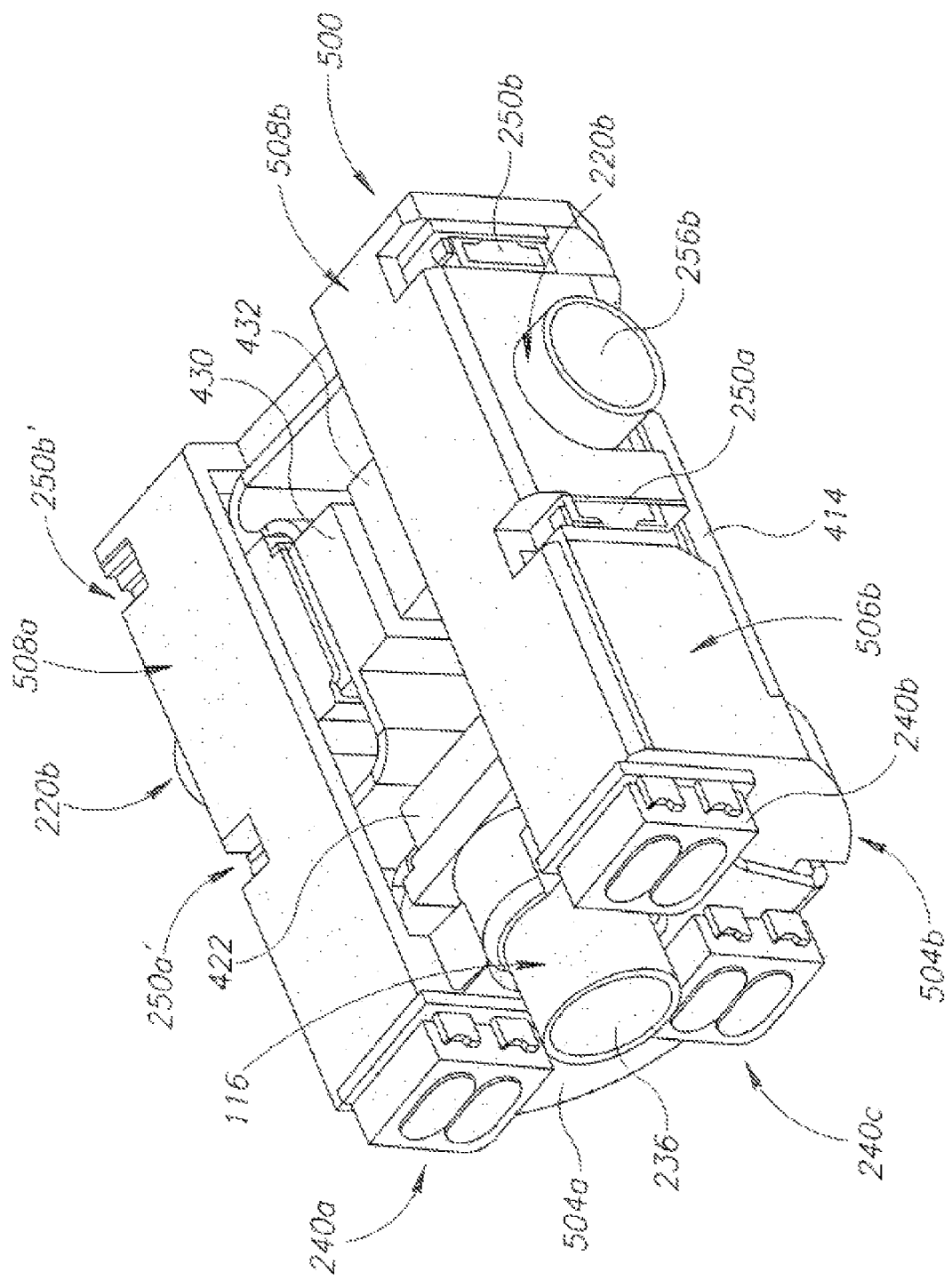
FIG. 6 schematically depicts an isometric view of a folded flexible electronic circuit board carrying cameras and illumination sources and a flexible electronic circuit board holder, according to an exemplary embodiment of the current invention.

Reference is now made to FIGS. 5 and 6 which schematically depict isometric views (FIG. 5 shows an exploded view) of a folded flexible electronic circuit board carrying cameras and illumination sources and a flexible electronic circuit board holder, according to an exemplary embodiment of the current invention.

Similar to FIG. 2, flexible electronic circuit board 400, shown in FIG. 5 in its folded configuration, is configured to carry forward looking camera 116; LEDs 240a, 240b and 240c positioned to illuminate essentially the Field Of View (FOV) of forward looking camera 116; side looking cameras 220b; LEDs 250a and 250b positioned to illuminate essentially the Field Of View (FOV) of side looking cameras 220b; side looking cameras 220a and LEDs 250a' and 250b' positioned to illuminate essentially the Field Of View (FOV) of side looking cameras 220a.

Flexible electronic circuit board holder 500 is adapted to hold flexible electronic circuit board 400 in its desired folded position, and secure the front and side looking cameras and their corresponding illuminators in place. As shown in FIG. 5, flexible electronic circuit board holder 500 is a unitary piece of rigid material, such as brass, stainless steel, aluminum or any other material.

According to some embodiments, the use of metal for the construction of the flexible electronic circuit board holder is important for electric conductivity and heat transfer purposes. The flexible electronic circuit board holder, according to embodiments of the invention, (such as flexible electronic circuit board holder 500) can be used as a heat sink for some or all of the electronic components located at the tip section, particularly illuminators (such as side or front LEDs) and reduce overall temperature of the endoscope tip. This may solve or at least mitigate a major problem of raised temperatures of endoscope tip and/or any of its components, particularly when using LED illuminators.

Flexible electronic circuit board holder 500 includes a back portion 502 adapted to support second side LED surface 436 and fourth side LED surface 440.

Flexible electronic circuit board holder 500 further includes front portions 504a and 504b, supporting the back sides (opposing to the sides where the LEDs are attached) of first front LED surface 408 and second front LED surface 410, respectively.

Flexible electronic circuit board holder 500 further includes two side portions 506a (not shown) and 506b on the two opposing sides of flexible electronic circuit board holder 500. Each of side portions 506a and 506b include two small openings for the side LEDs (250 a, 250b, 250a', 250b') and one opening for side looking camera 220b and 220a (not shown). Side portions 506a and 506b of flexible electronic circuit board holder 500 abut first and second side foldable panels 416 and 414, respectively, of flexible electronic circuit board 400.

Figure 7:
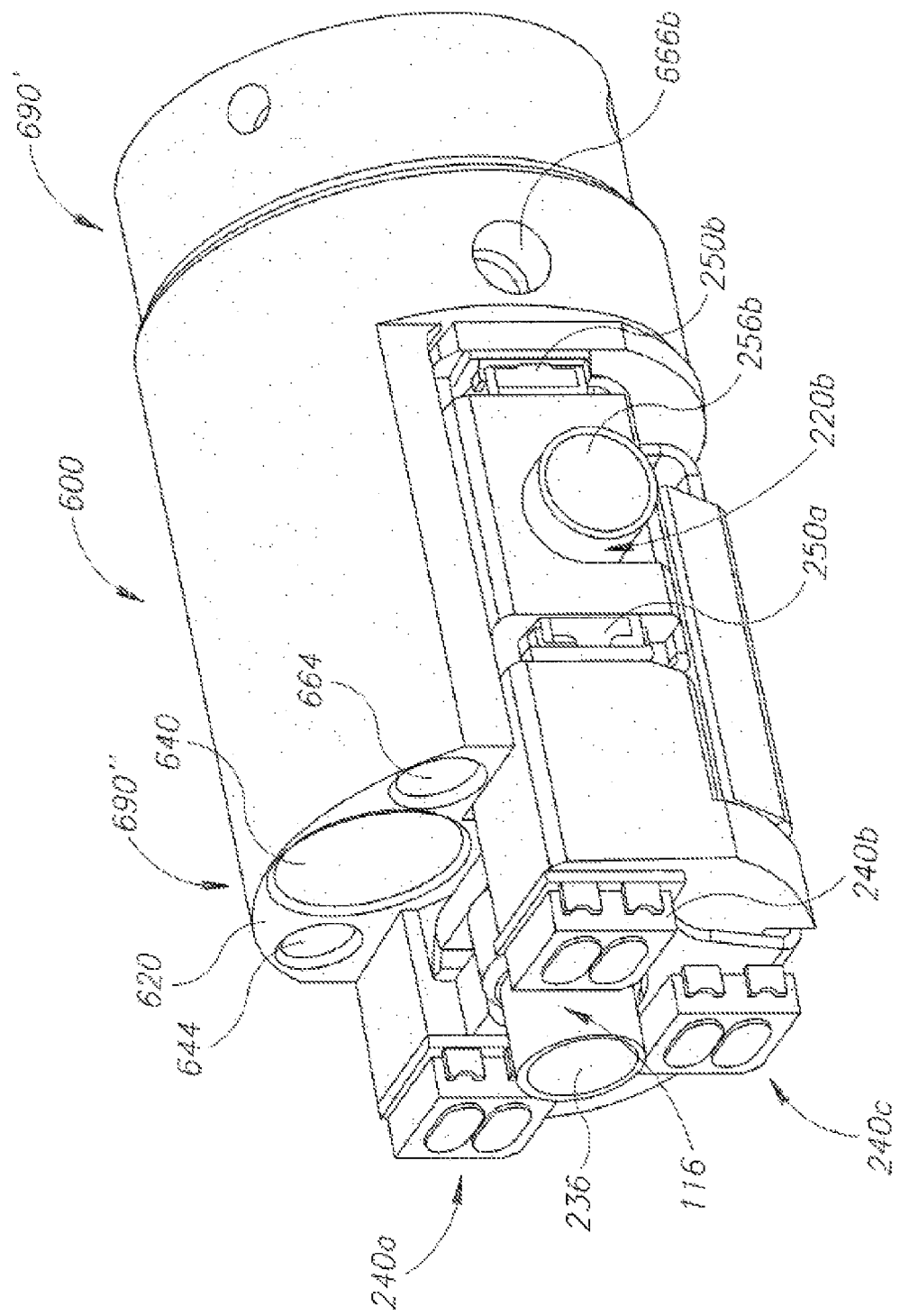
FIG. 7 schematically depicts an isometric view of a folded flexible electronic circuit board carrying cameras and illumination sources, a flexible electronic circuit board holder, and a fluid channeling component, according to an exemplary embodiment of the current invention; and, FIG. 8 schematically depicts an isometric view of a folded flexible electronic circuit board carrying cameras and illumination sources, a flexible electronic circuit board holder, a fluid channeling component, and a tip cover (in an exploded view), according to an exemplary embodiment of the current invention.

Flexible electronic circuit board holder 500 further includes a top part including top portions 508a and 508b (the top part of the flexible electronic circuit board holder may also include one top portion) covering the top part of flexible electronic circuit board 400 and configured to support fluid channeling component 600 (FIG. 7).

Reference is now made to FIG. 7, which schematically depicts an isometric view of a folded flexible electronic circuit board carrying cameras and illumination sources, a flexible electronic circuit board holder, and a fluid channeling component, according to an exemplary embodiment of the current invention. FIG. 6 schematically depicts an isometric view of a folded flexible electronic circuit board carrying cameras and illumination sources and a flexible electronic circuit board holder. FIG. 7 adds to the configuration of FIG. 6, a fluid channeling component 600, which includes irrigation and insufflation (I/I) channels, jet channel and a working channel. Fluid channeling component 600 is a separate component from flexible electronic circuit board 400. This configuration is adapted to separate the fluid channels and working channel, which are located in fluid channeling component 600 from the sensitive electronic and optical parts which are located in the area of flexible electronic circuit board 400.

Fluid channeling component 600 (or according to some embodiments, a unitary fluid channeling component), according to some embodiments, may generally include two parts: a proximal fluid channeling component section 690' and a distal fluid channeling component section 690". Proximal fluid channeling component section 690' may have an essentially cylindrical shape. Distal unitary channeling component section 690" may partially continue the cylindrical shape of proximal fluid channeling component section 690' and may have a shape of a partial cylinder (optionally elongated partial cylinder), having only a fraction of the cylinder (along the height axis of the cylinder), wherein another fraction of the cylinder (along the height axis of the cylinder) is missing. Distal fluid channeling component section 690" may be integrally formed as a unitary block with proximal fluid channeling component section 690'. The height of distal fluid channeling component section 690" may by higher than that of proximal fluid channeling component section 690'. In the case of distal fluid channeling component section 690", the shape of the partial cylinder (for example, partial cylinder having only a fraction of a cylinder shape along one side of the height axis) may provide a space to accommodate flexible electronic circuit board 400 and flexible electronic circuit board holder 500.

Front face 620 of distal fluid channeling component section 690" includes a distal opening 640 of working channel (located inside fluid channeling component 690, not shown). Front face 620 of distal fluid channeling component section 690" further includes distal opening 644 of a jet fluid channel which may be used for providing high pressure jet of fluid such as water or saline for cleaning the walls of the body cavity (such as the colon) and optionally for suction. Front face 620 of distal fluid channeling component section 690" further includes irrigation and insufflation (I/I) opening 664 which may be used for injecting fluid (liquid and/or gas) to wash contaminants such as blood, feces and other debris from front optical assembly 236 of forwards looking camera 116.

Proximal fluid channeling component section 690' of fluid channeling component 600 includes I/I openings 666a (not shown) and 666b aimed at side optical assembly 256a and 256b, respectively, and used for injecting fluid (the term "fluid" may also include gas and/or liquid) to wash contaminants such as blood, feces and other debris from side optical assemblies 256a and 256b of side looking cameras 220a and 220b. According to some embodiments, the injectors may supply liquid for cleaning any of the tip elements (such as any optical assembly, windows, LEDs, and other elements).

Figure 8:
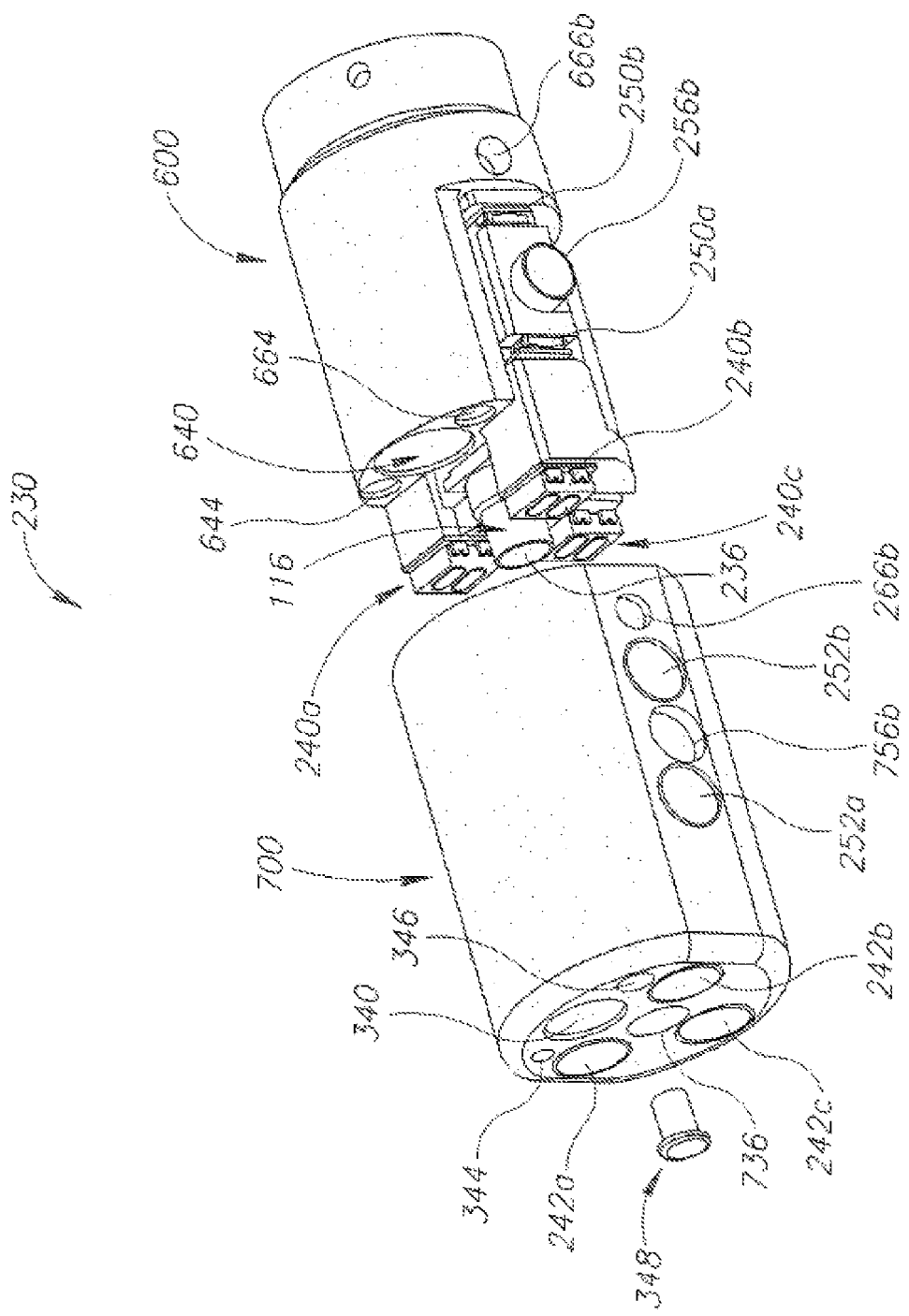

Reference is now made to FIG. 8, which schematically depicts an isometric view of a folded flexible electronic circuit board carrying cameras and illumination sources, a flexible electronic circuit board holder, a fluid channeling component, and a tip cover (in an exploded view), which together form a tip section of an endoscope, according to an exemplary embodiment of the current invention.

Fluid channeling component 600, flexible electronic circuit board 400 and flexible electronic circuit board holder 500 are described in FIGS. 6 and 7. Tip cover 700 is designed to fit over the inner parts of the tip section 230, and to provide protection to the internal components in the inner part.

Tip cover 700 includes hole 736 configured to align with front optical assembly 236 of forwards looking camera 116; optical windows 242a, 242b and 242c of LEDs 240a, 240b and 240c (seen for example in FIGS. 2 and 5-8); distal opening 340 of a working channel (not shown); distal opening 344 of a jet fluid channel; I/I injector 346 having a nozzle 348 (aligning with opening 664 of Fluid channeling component 600); holes 756a (not shown) and 756a configured to align with side optical assemblies 256a and 256b of side looking cameras 220a and 220b; optical windows 252a and 252b of LEDs 250a and 250b for camera 220a; and optical windows 252a' and 252b' of LEDs 250a' and 250b' for camera 220b; side holes 266a (not shown) and 266b adapted to align with I/I openings 666a (not shown) and 666b.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What we claim is:

1. An imaging module for an endoscope, comprising:
an optical assembly;
a flexible circuit board having a bent configuration and an unbent configuration, and wherein the flexible circuit board comprises:
  a distal section configured to hold the optical assembly and including a first distal portion, a second distal portion, an opening configured to receive the optical assembly, and a proximal portion coupled to the first and the second distal portions,
  wherein a central longitudinal axis of the proximal portion extends between the first and the second distal portions when in the unbent configuration,
  wherein, with the flexible circuit board in the unbent configuration, the proximal portion and the first and the second distal portions are substantially coplanar,
  wherein, with the flexible circuit board in the bent configuration, the first and the second distal portions extend transverse to the proximal portion, and
  wherein the first and the second distal portions are at a distalmost end of the flexible circuit board in the bent and the unbent configurations of the flexible circuit board;
a holder configured to hold the flexible circuit board, wherein the holder comprises:
  a first planar distal surface extending transverse to a central longitudinal axis of the imaging module;
  a second planar distal surface extending transverse to the central longitudinal axis of the imaging module; and
  a space extending between the first planar distal surface and the second planar distal surface, wherein the space is configured to receive the optical assembly; and
a fluid channeling component, wherein the holder is configured to support the fluid channeling component and the space is configured to receive a portion of the fluid channeling component;
wherein the opening is U-shaped, defined by edges of the first distal portion, the second distal portion, and the proximal portion; and wherein the opening is aligned with the space of the holder.

2. The imaging module of claim 1, wherein the first distal portion, the second distal portion, and the proximal portion form an arc shape configured to support the optical assembly; wherein the first planar distal surface is configured to hold the first distal portion; and wherein the second planar distal surface is configured to hold the second distal portion.

3. The imaging module of claim 1, wherein:
the flexible circuit board further includes an intermediate section proximal to the distal section, wherein the intermediate section includes a center portion, a first side panel, and a second side panel, wherein the first side panel and the second side panel are angled relative to the center portion when the flexible circuit board is in the bent configuration; and
the optical assembly includes an optical axis, wherein the optical axis extends in a plane substantially perpendicular to the distal section when the flexible circuit board in the bent configuration.

4. The imaging module of claim 1, wherein the flexible circuit board further includes an intermediate section proximal to the distal section, the intermediate section including a central portion, a first lateral portion, and a second lateral portion on an opposite side of the central portion as the first lateral portion; wherein the second lateral portion includes an arm portion, and wherein the arm portion includes a surface configured to carry a camera of the optical assembly.

5. The imaging module of claim 4, wherein, with the flexible circuit board in the unbent configuration, the distal and the intermediate sections are substantially coplanar.

6. The imaging module of claim 4, wherein, with the flexible circuit board in the unbent configuration, the central portion, the first lateral portion, and the second lateral portion are substantially coplanar, and
wherein, with the flexible circuit board in the bent configuration, the surface of the arm portion is substantially parallel to the distal section and is distal to the first planar distal surface and the second planar distal surface.

7. The imaging module of claim 4, wherein, with the flexible circuit board in the bent configuration, the surface of the arm portion is positioned proximal to and between the first and second distal portions of the distal section.

8. The imaging module of claim 7, wherein an optical axis of the optical assembly extends perpendicular to and intersects the surface of the arm portion.

9. The imaging module of claim 4, wherein with the flexible circuit board in the bent configuration, the first lateral portion of the intermediate section extends substantially perpendicular to the first and second distal portions of the distal section.

10. The imaging module of claim 4, wherein the flexible circuit board further includes a proximal section proximal to the intermediate section, and wherein a proximal portion of the holder includes a proximalmost planar surface extending transverse to the longitudinal axis of the imaging module.

11. The imaging module of claim 10, wherein, with the flexible circuit board in the unbent configuration, the distal, the intermediate, and the proximal sections are substantially coplanar.

12. The imaging module of claim 11, wherein portions of the proximal section pivot about a plurality of pivot axes, such that the proximal section includes a plurality of bends.

13. The imaging module of claim 1, wherein the holder includes a proximalmost planar surface; and wherein the fluid channeling component includes a distal-facing surface configured to mate with the proximalmost planar surface of the holder.

14. The imaging module of claim 1, wherein a distalmost end of the holder is distal to a distalmost end of the fluid channeling component.

15. An imaging module for an endoscope, comprising:
an optical assembly;
a flexible circuit board having a plurality of bends, wherein the flexible circuit board comprises:
a front section configured to support the optical assembly and including a U-shaped portion configured to receive the optical assembly,
an intermediate section, and
a rear section, wherein portions of the front, the intermediate, and the rear sections have a first wall thickness, wherein a portion of the intermediate section has a second wall thickness, wherein a portion of the rear section has a third wall thickness, wherein the second and the third wall thicknesses are thicker than the first wall thickness, wherein the portion of the intermediate section with the second wall thickness is centered with respect to the U-shaped portion; and
a holder configured to hold the flexible circuit board, wherein the holder comprises:
a first planar distal surface at a distalmost end of the holder and extending transverse to a central longitudinal axis the imaging module;
a second planar distal surface at the distalmost end of the holder and extending transverse to the central longitudinal axis of the imaging module;
a first planar intermediate surface extending proximally from the first planar distal surface to a proximalmost end of the holder;
a second planar intermediate surface extending proximally from the second planar distal surface to the proximalmost end of the holder; and
a space extending 1) between the first planar distal surface and the second planar distal surface and 2) between the first planar intermediate surface and the second planar intermediate surface, wherein the space is configured to receive the optical assembly; and
a fluid channeling component, wherein the holder is configured to support the fluid channeling component and the space is configured to receive a portion of the fluid channeling component.

16. The imaging module of claim 15, wherein the flexible circuit board has a bent configuration and an unbent configuration, and wherein in the unbent configuration of the flexible circuit board, a plurality of surfaces of the front, the intermediate, and the rear sections face: (i) the third direction and (ii) opposite the third direction, and wherein with the flexible circuit board in the bent configuration, the plurality of surfaces face: (i) the first direction and (ii) the second direction, and the portion of the rear section having the third wall thickness is perpendicular to the portion of the intermediate section having the second wall thickness.

17. The imaging module of claim 16, wherein, with the flexible circuit board in the bent configuration, first portions of the front, the intermediate, and the rear sections of the flexible circuit board face the first direction, and second portions of the front, the intermediate, and the rear sections project in the third direction from the first portions.

18. An imaging module for an endoscope, comprising:
an optical assembly;
a flexible circuit board having a bent configuration and an unbent configuration, and wherein the flexible circuit board comprises:
a distal section configured to hold the optical assembly and including a first distal portion, a second distal portion, an opening configured to receive the optical assembly, and a proximal portion coupled to the first and the second distal portions,
wherein a central longitudinal axis of the proximal portion extends between the first and the second distal portions when in the unbent configuration,
wherein, with the flexible circuit board in the unbent configuration, the proximal portion and the first and the second distal portions are substantially coplanar,
wherein, with the flexible circuit board in the bent configuration, the first and the second distal portions extend transverse to the proximal portion, and
wherein the first and the second distal portions are at a distalmost end of the flexible circuit board in the bent and the unbent configurations of the flexible circuit board;
a holder configured to hold the flexible circuit board, wherein the holder comprises:
a first planar distal surface extending transverse to a central longitudinal axis of the imaging module;
a second planar distal surface extending transverse to the central longitudinal axis of the imaging module; and
a space extending between the first planar distal surface and the second planar distal surface, wherein the space is configured to receive the optical assembly; and
a fluid channeling component, wherein the holder is configured to support the fluid channeling component and the space is configured to receive a portion of the fluid channeling component;
wherein the holder includes a proximalmost planar surface; and wherein the fluid channeling component includes a distal-facing surface configured to mate with the proximalmost planar surface of the holder.

19. The imaging module of claim 18, wherein a distalmost end of the holder is distal to a distalmost end of the fluid channeling component.

20. The imaging module of claim 18, wherein:
the flexible circuit board further includes an intermediate section proximal to the distal section, wherein the intermediate section includes a center portion, a first side panel, and a second side panel, wherein the first side panel and the second side panel are angled relative to the center portion when the flexible circuit board is in the bent configuration; and
the optical assembly includes an optical axis, wherein the optical axis extends in a plane substantially perpendicular to the distal section when the flexible circuit board in the bent configuration.

* * * * *